(12) United States Patent
Usui et al.

(10) Patent No.: US 7,122,310 B2
(45) Date of Patent: Oct. 17, 2006

(54) METHODS OF CONSTRUCTING SELF-ASSEMBLY OF PROBES AND METHOD OF DETECTING THE SAME

(75) Inventors: Mitsugu Usui, Abiko (JP); Mari Mitsuka, Kashiwa (JP); Chikako Hakii, Kashiwa (JP)

(73) Assignee: Sanko Junyaku Co., Ltd., Tokyo (JP)

( * ) Notice: Subject to any disclaimer, the term of this patent is extended or adjusted under 35 U.S.C. 154(b) by 416 days.

(21) Appl. No.: 10/149,187

(22) PCT Filed: Oct. 5, 2001

(86) PCT No.: PCT/JP01/08806

§ 371 (c)(1),
(2), (4) Date: Jun. 10, 2002

(87) PCT Pub. No.: WO02/31192

PCT Pub. Date: Apr. 18, 2002

(65) Prior Publication Data

US 2003/0087262 A1    May 8, 2003

(30) Foreign Application Priority Data

Oct. 11, 2000   (JP)   .............................. 2000-311151

(51) Int. Cl.
*C12Q 1/68*     (2006.01)
*C12P 19/34*    (2006.01)
*C07H 21/04*    (2006.01)

(52) U.S. Cl. ........................ 435/6; 435/91.2; 536/23.1; 536/24.3; 536/24.33

(58) Field of Classification Search ................. 435/6, 435/91.2; 536/22.1, 24.3, 24.33
See application file for complete search history.

(56) References Cited

U.S. PATENT DOCUMENTS

| | | | |
|---|---|---|---|
| 5,175,270 A | 12/1992 | Nilsen et al. | |
| 5,437,977 A | 8/1995 | Segev | ............................ 435/6 |
| 5,487,973 A | 1/1996 | Nilsen et al. | ................... 435/6 |
| 5,605,793 A | 2/1997 | Stemmer | ......................... 435/6 |
| 6,261,846 B1 * | 7/2001 | Usui | .............................. 435/6 |

FOREIGN PATENT DOCUMENTS

| | | |
|---|---|---|
| EP | 0 450 594 | 10/1991 |
| EP | 1 002 877 | 5/2000 |
| JP | 7-88000 | 4/1995 |
| JP | 10-500561 | 1/1998 |
| JP | 2000-201687 | 7/2000 |
| WO | 95/22625 | 8/1995 |
| WO | WO 99/06595 | 2/1999 |

OTHER PUBLICATIONS

Ratilainen et al., "Hybridization of Peptide Nucleic Acid", *Biochemistry*, vol. 37, pp. 12331-12342, 1998.
Prehn, "Hybridization of Uracil pentanucleotides with Poly-dA", *Acta biol. Med. Germ.*, vol. 31, pp. 885-887, 1973, in German with English translation thereof.

* cited by examiner

*Primary Examiner*—Kenneth R. Horlick
*Assistant Examiner*—Joyce Tung
(74) *Attorney, Agent, or Firm*—Wenderoth, Lind & Ponack, L.L.P.

(57) ABSTRACT

The present invention provides a novel method for forming a self-assembly substance of probes making it possible to shorten a reaction time required for formation of a self-assembly substance and also to increase regions of probes available for detection of a target gene by previously preparing a plurality of dimer-probes and increasing the types. This method comprises the steps of: providing plural groups, wherein each group includes a pair of dimer forming probes containing a pair of oligonucleotides, each oligonucleotide having three regions of a 3' side region, a mid-region and a 5' side region, in which the mid-regions of the oligonucleotides have base sequences complementary to each other, and the 3' side regions and the 5' side regions of the oligonucleotides have base sequences not complementary to each other; hybridizing a plurality of pairs of the dimer forming probes of the plural groups; and forming a double-stranded self-assembly substance by self-assembly of the oligonucleotides.

16 Claims, 16 Drawing Sheets

(a) First group (b) Second group (a)

(b)

Formation of self-assembly substance (a) First group (b) Second group (a) First group (b) Second group (c) Third group (a)

(b)

Formation of self-assembly substance (a) First group

(b) Second group

(c) Third group

(d) Fourth group

(a)

Formation of self-assembly substance (b)

(a) First group

(b) Second group

(c) Third group

(d) Fourth group

Formation of self-assembly substance (a) First group

(b) Second group

(c) Third group

(d) Fourth group

(e) Fifth group

0.5% agarose gel 0.5% agarose gel

| Lane 1: Experimental example 1 |
| Lane 2: Experimental example 2 |
| Lane 3: Experimental example 5 |
| Lane 4: Experimental example 3 |
| Lane 5: Experimental example 4 |
| Lane 6: Experimental example 6 |
| M      : DNA size marker |

```
                           SEQUENCE LISTING

<160> NUMBER OF SEQ ID NOS: 10

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 1
gtgctgactt aaccggatac gaacaggatc ctagacctag catagtacag tccgatggtg      60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 2
cctcaagacg catgtctttc ctaggtctag gatcctgttc ctagaacgga ctgtacttcg      60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 3
gaaagacatg cgtcttgagg ctatccgttc gacttgcatg cgaagtacag tccgttctag      60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 4
gtatccggtt aagtcagcac catgcaagtc gaacggatag caccatcgga ctgtactatg      60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 5
gtgctgactt aaccggatac gaacaggatc ctagacctag catagtacag tccgatggtg      60

<210> SEQ ID NO 6
<211> LENGTH: 60
<212> TYPE: DNA
<213> ORGANISM: Artificial Sequence
```

```
<220> FEATURE:
<223> OTHER INFORMATION: Description of Artificial Sequence: synthesized
      probe

<400> SEQUENCE: 6
cctcaagacg catgtctttc ctaggtctag gatcctgttc ctagaacgga ctgtacttcg      60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 7
gaaagacatg cgtcttgagg ctatccgttc gacttgcatg ctagacgctt cttgcgtaag      60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 8
gtgtcgaatt gacactcagc catgcaagtc gaacggatag caccatcgga ctgtactatg      60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 9
gctgagtgtc aattcgacac gcaccctatc aggcagtatc cgaagtacag tccgttctag      60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: synthesized
      probe

<400> SEQUENCE: 10
gtatccggtt aagtcagcac gatactgcct gatagggtgc cttacgcaag aagcgtctag      60
```

METHODS OF CONSTRUCTING SELF-ASSEMBLY OF PROBES AND METHOD OF DETECTING THE SAME

TECHNICAL FIELD

The present invention relates to a plurality of dimer forming probes containing a pair of oligonucleotides, a method for forming a self-assembly substance of the dimer forming probes, a formed self-assembly substance, and a method for detecting the formed self-assembly substance.

BACKGROUND ART

In the method for forming a self-assembly substance of probes in which a double-stranded self-assembly substance is formed by providing a plurality of pairs of probes each comprising n (n≧3) portions complementary to each other (may be referred to as a "HoneyComb probe: HCP" hereinafter) and hybridizing the probes so as to cross alternately (see U.S. Pat. No. 6,261,846, JP A 00-201687, and Japanese Patent Application No. 2000-98797, and this method may be referred to as a "PALSAR (Probe alternation link self-assembly reaction) method" hereinafter), a target gene is detected through formation of a double-stranded self-assembly substance by using only a pair of oligonucleotide probes and hybridizing the probes so as to cross-link alternately, but as only two oligonucleotide probes are used, there are several restrictions in regions of the oligonucleotide probes be used for detection of a target gene and regions for labeling with a fluorescent dye, an enzyme or an antibody.

Furthermore, as two oligonucleotide probes react to each other alternately, each region is in competition with each other, and a somewhat long reaction time is required for formation of a self-assembly substance.

In a pair of oligonucleotide probes used in the PALSAR method, only a pair of oligonucleotide probes are used and hybridized to each other so as to cross-link alternately, thereby forming a double-stranded self-assembly substance.

It is an object of the present invention to provide a novel method for forming a self-assembly substance of probes in which not only a pair of oligonucleotide probes, but each oligonucleotide probe is previously prepared as a plurality of dimer-probes, and the types are increased, thereby enabling a reaction time required for formation of a self-assembly substance to be further shortened and enabling regions of oligonucleotide probes which can be used for detection of a target gene and regions for labeling with a fluorescent dye, an enzyme or an antibody to be increased, and a method for detecting the self-assembly substance formed by the method for forming the self-assembly substance.

In the recent techniques for genetic diagnosis, various techniques represented by an enzyme immunoassay called EIA and a fluorescent labeling are used to detect a target gene, but in any method, use of an expensive enzyme, an antibody or fluorescent label and complicated operations are required.

DISCLOSURE OF THE INVENTION

To solve the problems described above, a method for forming a self-assembly substance according to the present invention comprise, in a first aspect, the steps of: providing a first group and a second group, wherein each group includes a pair of dimer forming probes containing a pair of oligonucleotides No. 1 and No. 2, each oligonucleotide having three regions of a 3', side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the first group and the 3' side region of the oligonucleotide No. 2 of the second group, (b) the 5' side region of the oligonucleotide No. 2 of the first group and the 5' side region of the oligonucleotide No. 1 of the second group, (c) the 3' side region of the oligonucleotide No. 1 of the second group and the 3' side region of the oligonucleotide No. 2 of the first group, and (d) the 5' side region of the oligonucleotide No. 2 of the second group and the 5' side region of the oligonucleotide No. 1 of the first group have base sequences complementary to each other, respectively; hybridizing a plurality of pairs of the dimer forming probes of the first and second groups; and forming a double-stranded self-assembly substance by self-assembly of the oligonucleotides.

A method for forming a self-assembly substance according to the present invention comprise, in a second aspect, the steps of: providing a first group and a second group, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the first group and the 3' side region of the oligonucleotide No. 1 of the second group, (b) the 5' side region of the oligonucleotide No. 2 of the first group and the 5' side region of the oligonucleotide No. 1 of the second group, (c) the 3' side region of the oligonucleotide No. 2 of the second group and the 3' side region of the oligonucleotide No. 2 of the first group, and (d) the 5' side region of the oligonucleotide No. 2 of the second group and the 5' side region of the oligonucleotide No. 1 of the first group have base sequences complementary to each other, respectively; hybridizing a plurality of pairs of the dimer forming probes of the first and second groups; and forming a double-stranded self-assembly substance by self-assembly of the oligonucleotides.

A method for forming a self-assembly substance according to the present invention comprise, in a third aspect, the steps of: providing plural groups from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the (n−1)th group and the 3' side region of the oligonucleotide No. 2 of the nth group, (b) the 5' side region of the oligonucleotide No. 2 of the (n−1)th group and the 5' side region of the oligonucleotide No. 1 of the nth group, (c) the 3' side region of the oligonucleotide No. 1 of the last group and the 3' side region of the oligonucleotide No. 2 of the first group, and (d) the 5' side region of the oligonucleotide No. 2 of the last group and the 5' side region of the oligonucleotide No. 1 of the first group have base sequences complementary to each other, respectively; hybridizing a plurality of pairs of the dimer forming probes of the first group to the nth group; and forming a double-stranded self-assembly substance by self-assembly of the oligonucleotides.

A method for forming a self-assembly substance according to the present invention comprise; in a fourth aspect, the steps of: providing plural groups from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the (n−1)th group and the 3' side region of the oligonucleotide No. 2 of the nth group, (b) the 5' side region of the oligonucleotide No. 1 of the (n−1)th group and the 5' side region of the oligonucleotide No. 2 of the nth group, (c) the 3' side region of the oligonucleotide No. 1 of the last group and the 3' side region of the oligonucleotide No. 2 of the first group, and (d) the 5' side region of the oligonucleotide No. 1 of the last group and the 5' side region of the oligonucleotide No. 2 of the first group have base sequences complementary to each other, respectively; hybridizing a plurality of pairs of the dimer forming probes of the first group to the nth group; and forming a double-stranded self-assembly substance by self-assembly of the oligonucleotides.

By arranging at least one G (guanine) or C (cytosine) at one or more ends of the three regions of the dimer forming probes and forming at least one G-C bond at the ends of the regions in hybridizing the dimer forming probes, it is made possible to form s stable double-stranded self-assembly substance.

A nucleic acid constituting the dimer forming probes is composed usually of DNA or RNA, but may be a nucleic acid analogue. The nucleic acid analogue includes, for example, peptide nucleic acid (PNA, WO 92/20702) and Locked Nucleic Acid (LNA, Koshkin AA et al. *Tetrahedron* 1998. 54, 3607–3630., Koshkin AA et al. *J. Am. Chem. Soc.* 1998. 120, 13252–13253., Wahlestedt C et al. *PNAS.* 2000. 97, 5633–5638.). Further, a pair of the dimer forming probes are composed usually of the same type of nucleic acids, but, for example, a pair of DNA and RNA probes may be used. That is, the type of nucleic acids in the probes can be selected from DNA, RNA or nucleic acid analogues (e.g., PNA, LNA, etc.). Furthermore, the nucleic acid composition in one probe is not required to consist of only one kind of nucleic acids (e.g., DNA only), and as necessary, for example, a probe (a chimera probe) composed of DNA and RNA may be usable, which is within the scope of the present invention.

In hybridizing a plurality of pairs of the dimer forming probes, it is preferable to previously form dimer-probes with a plurality of pairs of the dimer forming probes and then hybridize the dimer-probes formed for each group.

A self-assembly substance according to the present invention is formed by the method for forming a self-assembly substance. A stacking of bases in the self-assembly substance formed by the method for forming the self-assembly substance according to the present invention has a regular higher-order structure bringing about a hypochromic effect called "hypochromism" reducing the intensity of an absorption band in the ultraviolet region at 260 nm, thereby confirming the state of the self-assembly substance. Furthermore, an inexpensive fluorescent material is inserted between stacked bases of the self-assembly substance to cause a change in fluorescence intensity, thereby confirming the state of the self-assembly substance. Thus, the method for forming a self-assembly substance according to the present invention is a technique that is excellent in cost-performance and makes it possible to easily detect genes at unprecedentedly low-cost.

A method for detecting a self-assembly substance according to the present invention is, in a first aspect, characterized in that a self-assembly substance formed by the method for forming a self-assembly substance is detected by utilizing a change in photochemical absorption to ultraviolet ray of the self-assembly substance.

A method for detecting a self-assembly substance according to the present invention is, in a second aspect, characterized in that a self-assembly substance formed by the method for forming a self-assembly substance is detected by adding a fluorescent substance having the property of bonding to a nucleic acid to base pairs of the self-assembly substance and checking photochemical change of the fluorescent substance.

A dimer forming probes according to the present invention is, in a first aspect, formed from a first group to a second group, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the first group and the 3' side region of the oligonucleotide No. 2 of the second group, (b) the 5' side region of the oligonucleotide No. 2 of the first group and the 5' side region of the oligonucleotide No. 1 of the second group, (c) the 3' side region of the oligonucleotide No. 1 of the second group and the 3' side region of the oligonucleotide No. 2 of the first group, and (d) the 5' side region of the oligonucleotide No. 2 of the second group and the 5' side region of the oligonucleotide No. 1 of the first group have base sequences complementary to each other, respectively.

A dimer forming probes according to the present invention is, in a second aspect, formed from a first group to a second group, wherein each group includes a pair of dimer forming probes containing a pair of oligonucleotides No. 1 and No. 2, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the first group and the 3' side region of the oligonucleotide No. 1 of the second group, (b) the 5' side region of the oligonucleotide No. 2 of the first group and the 5' side region of the oligonucleotide No. 1 of the second group, (c) the 3' side region of the oligonucleotide No. 2 of the second group and the 3' side region of the oligonucleotide No. 2 of the first group, and (d) the 5' side region of the oligonucleotide No. 2 of the second group and the 5' side region of the oligonucleotide No. 1 of the first group have base sequences complementary to each other, respectively.

A dimer forming probes according to the present invention is, in a third aspect, formed plural groups from a first group to an nth (n is an even number of 2 or more) group in turn, wherein each group includes a pair of dimer forming probes containing a pair of oligonucleotides No. 1 and No.

2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the (n−1)th group and the 3' side region of the oligonucleotide No. 2 of the nth group, (b) the 5' side region of the oligonucleotide No. 2 of the (n−1)th group and the 5' side region of the oligonucleotide No. 1 of the nth group, (c) the 3' side region of the oligonucleotide No. 1 of the last group and the 3' side region of the oligonucleotide No. 2 of the first group, and (d) the 5' side region of the oligonucleotide No. 2 of the last group and the 5' side region of the oligonucleotide No. 1 of the first group have base sequences complementary to each other, respectively.

A dimer forming probes according to the present invention is, in a fourth aspect, formed plural groups from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the (n−1)th group and the 3' side region of the oligonucleotide No. 2 of the nth group, (b) the 5' side region of the oligonucleotide No. 1 of the (n−1)th group and the 5' side region of the oligonucleotide No. 2 of the nth group, (c) the 3' side region of the oligonucleotide No. 1 of the last group and the 3' side region of the oligonucleotide No. 2 of the first group, and (d) the 5' side region of the oligonucleotide No. 1 of the last group and the 5' side region of the oligonucleotide No. 2 of the first group have base sequences complementary to each other, respectively.

It is preferable to arrange at least one G (guanine) or C (cytosine) at one or more ends of the three regions of the dimer forming probes.

The dimer forming probes are composed of DNA, RNA, PNA and/or LNA.

A dimer-probe according to the present invention is formed by hybridizing a pair of the dimer forming probes.

BEST MODE FOR CARRYING OUT THE INVENTION

Embodiments of the present invention are described below with reference to the attached drawings, and it is needless to say that these embodiments are given for an illustrative purpose and that various modifications are possible within a scope of the technical concept of the present invention.

In the present invention, plural sets of pairs of dimer forming probes are used, and the probes are reacted with each other under isothermal conditions in the absence of enzymes, thereby forming a self-assembly substance. The number of dimer forming probes to be used is not particularly limited, but preferably in the range of $10^2$ to $10^{15}$ probes. The composition and concentration of the buffering solution used in the reaction are not particularly limited, and a buffering solution used ordinarily in a nucleic acid amplification technique can be preferably employed. The pH may also be suitable in the common range, preferably in the range of pH 7.0 to pH 9.0. The reaction temperature is 40 to 90° C., preferably 55 to 65° C. These conditions are not particularly limited.

Illustrating the constitution of the present invention using a more specific example, the length (the number of bases) of each of the regions in one dimer forming probe may be the same or different.

And the length of each of the regions in one dimer forming probe as the number of bases is at least 5 bases, preferably at least 8, more preferably 10 to 100 bases, and still further preferably 15 to 30 bases.

Examples of formation of a self-assembly substance with the dimer forming probes according to the present invention are described below.

1. The first example of formation of a self-assembly substance with two sets of dimer forming probes.

Figure 1:
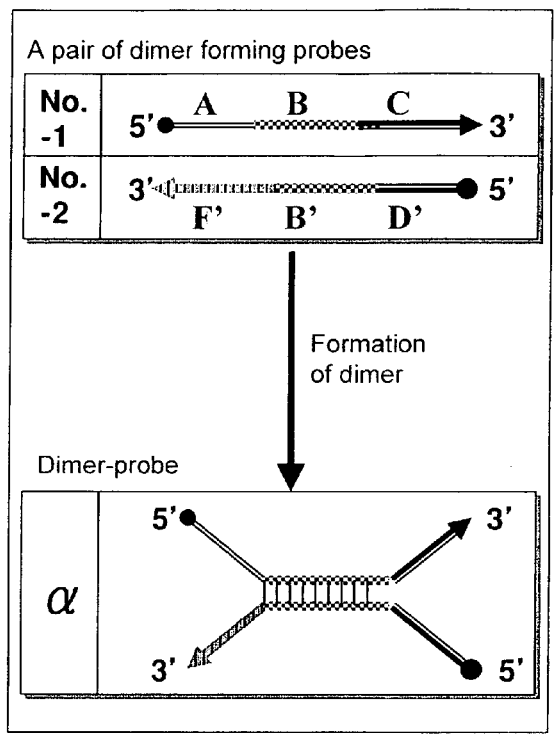
FIG. 1 is a schematic view showing an example of formation of two sets of dimer-probes in the method for forming the self-assembly substance according to the present invention, and in this figure are shown formation of a dimer-probe with a pair of dimer forming probes of a first group at (a), and formation of a dimer-probe with a pair of dimer forming probes of a second group at (b), respectively.
Figure 1:
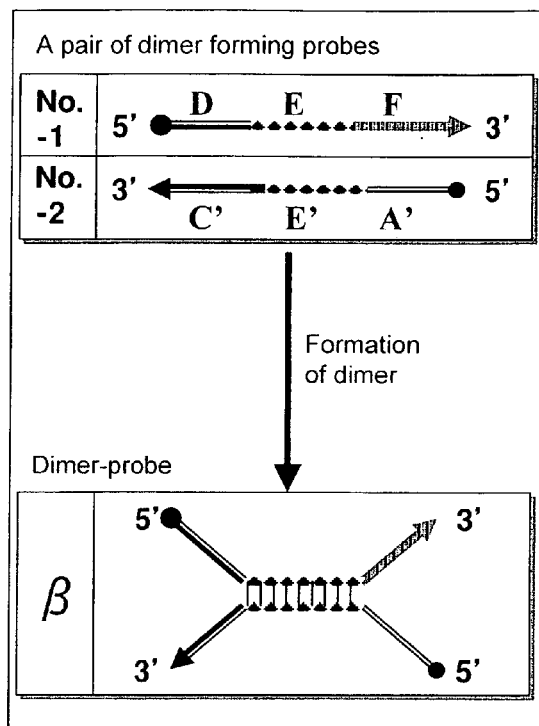

As shown at (a) in FIG. 1, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β) have constitution as described above ((b) in FIG. 1).

Figure 2:
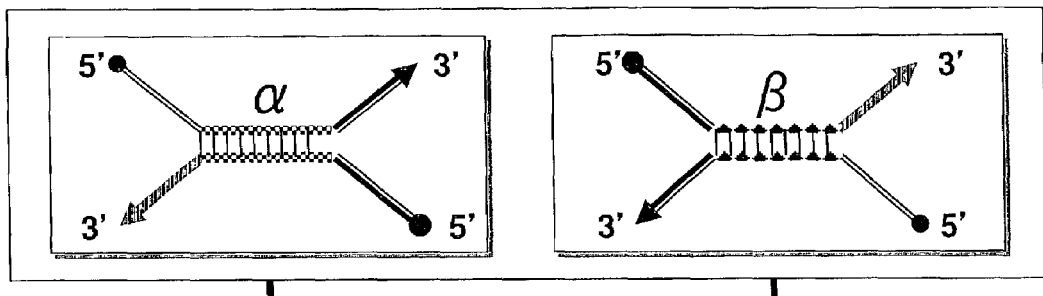
FIG. 2 is a schematic view showing an example of formation of a self-assembly substance with the two sets of dimer-probes shown in FIG. 1, and in this figure are shown the two sets of dimer-probes at (a), and a formed self-assembly substance at (b), respectively.
Figure 2:
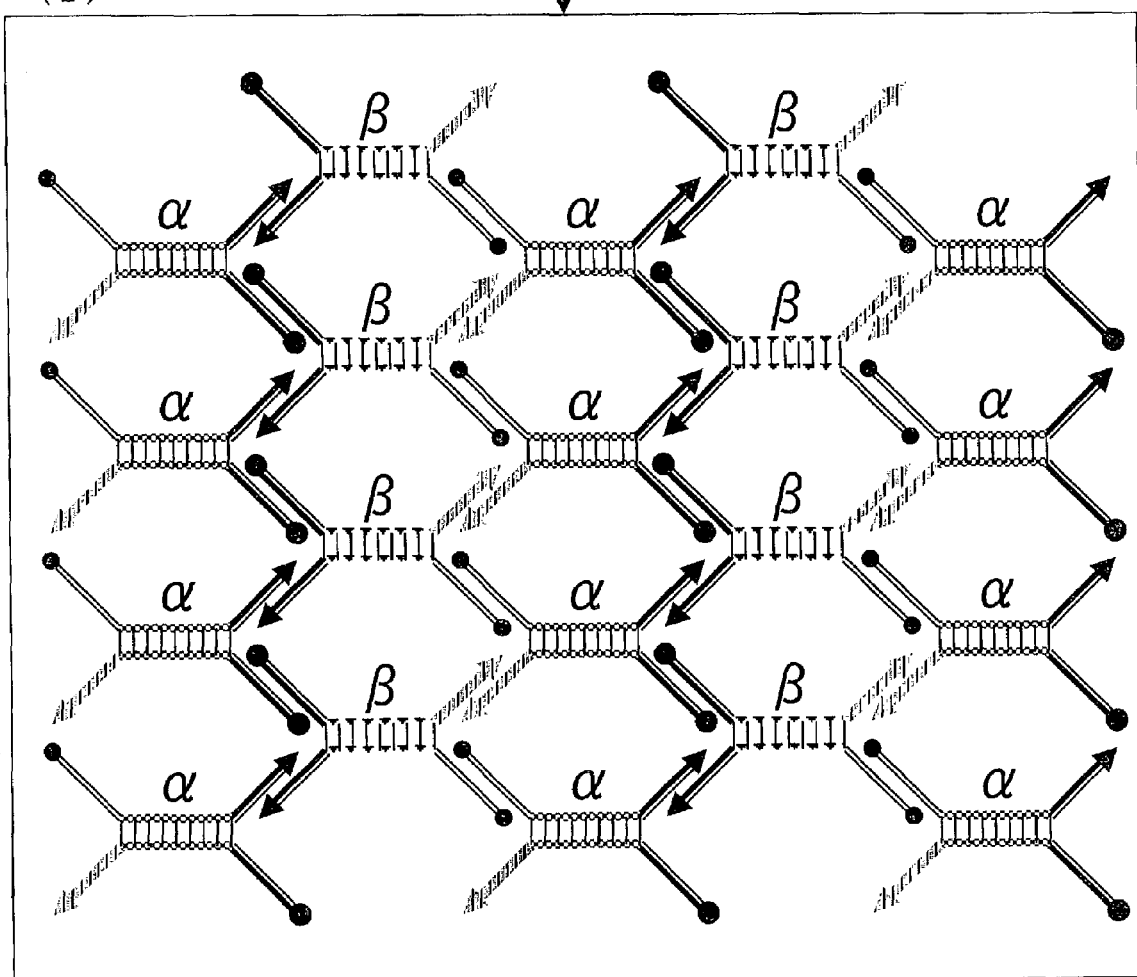

In the dimer-probe of the first group (α) and the dimer-probe of the second group (β), as shown in FIG. 1 and at (a) in FIG. 2, the 3' side region of the oligonucleotide No.1 of the dimer-probe (α) and the 3' side region of the oligonucleotide No. 2 of the dimer-probes (β), the 5' side region of the oligonucleotide No. 2 of the dimer-probe (α) and the 5' side region of the oligonucleotide No. 1 of the dimer-probes (β), the 3' side region of the oligonucleotide No. 2 of the dimer-probes (α) and the 3' side region of the oligonucleotide No. 1 of the dimer-probe (β), and the 5' side region of the oligonucleotide No. 1 of the dimer-probes (α) and the 5' side region of the oligonucleotide No. 2 of the dimer-probe (β) have base sequences complementary to each other, respectively. Thus by hybridizing the dimer-probes (α) and (β) to each other, the oligonucleotides are self-assembled to form a double-stranded self-assembly substance ((b) in FIG. 2).

2. The second example of formation of a self-assembly substance with two sets of dimer forming probes.

Figure 3:
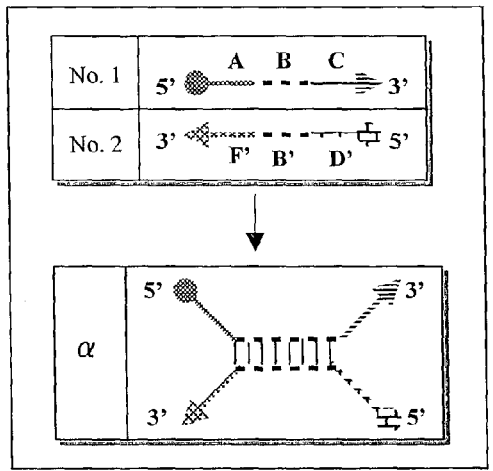
FIG. 3 is a schematic view showing another example of formation of two sets of dimer-probes in the method for forming the self-assembly substance according to the present invention, and in this figure are shown formation of a dimer-probe with a pair of dimer forming probes of a first group at (a), and formation of a dimer-probe with a pair of dimer forming probes of a second group at (b), respectively.
Figure 3:
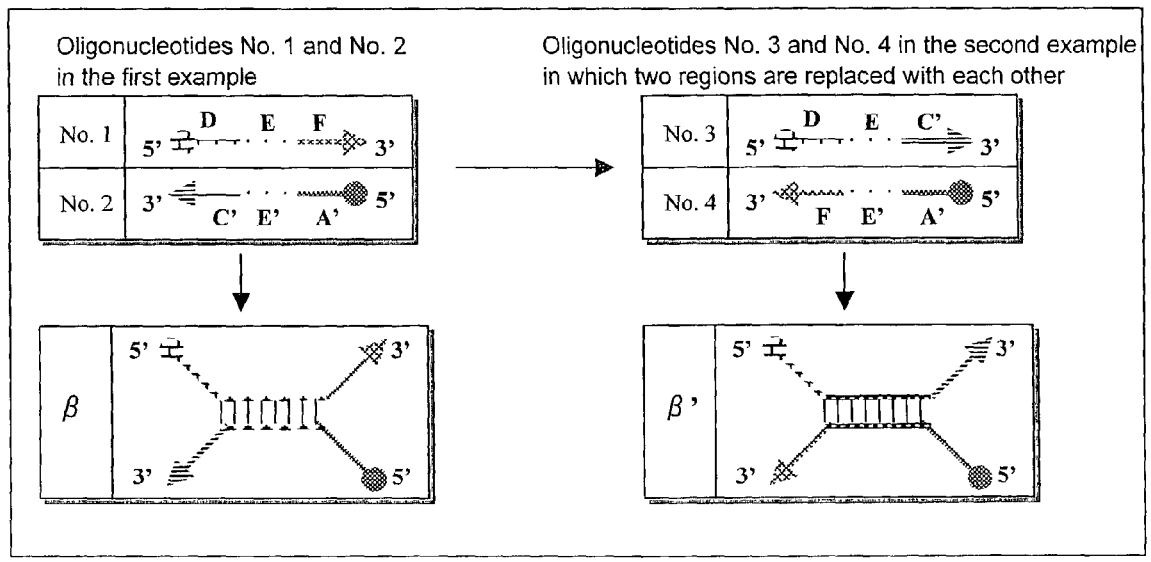

As the second example of formation of a self-assembly substance with two sets of dimer forming probes, it is possible to exchange the 3' side region or 5' side region in the oligonucleotide No. 1 of dimer forming probes of the second group with the 3' side region or 5' side region in the oligonucleotide No. 2 thereof, as shown at (b) in FIG. 3.

Figure 4:
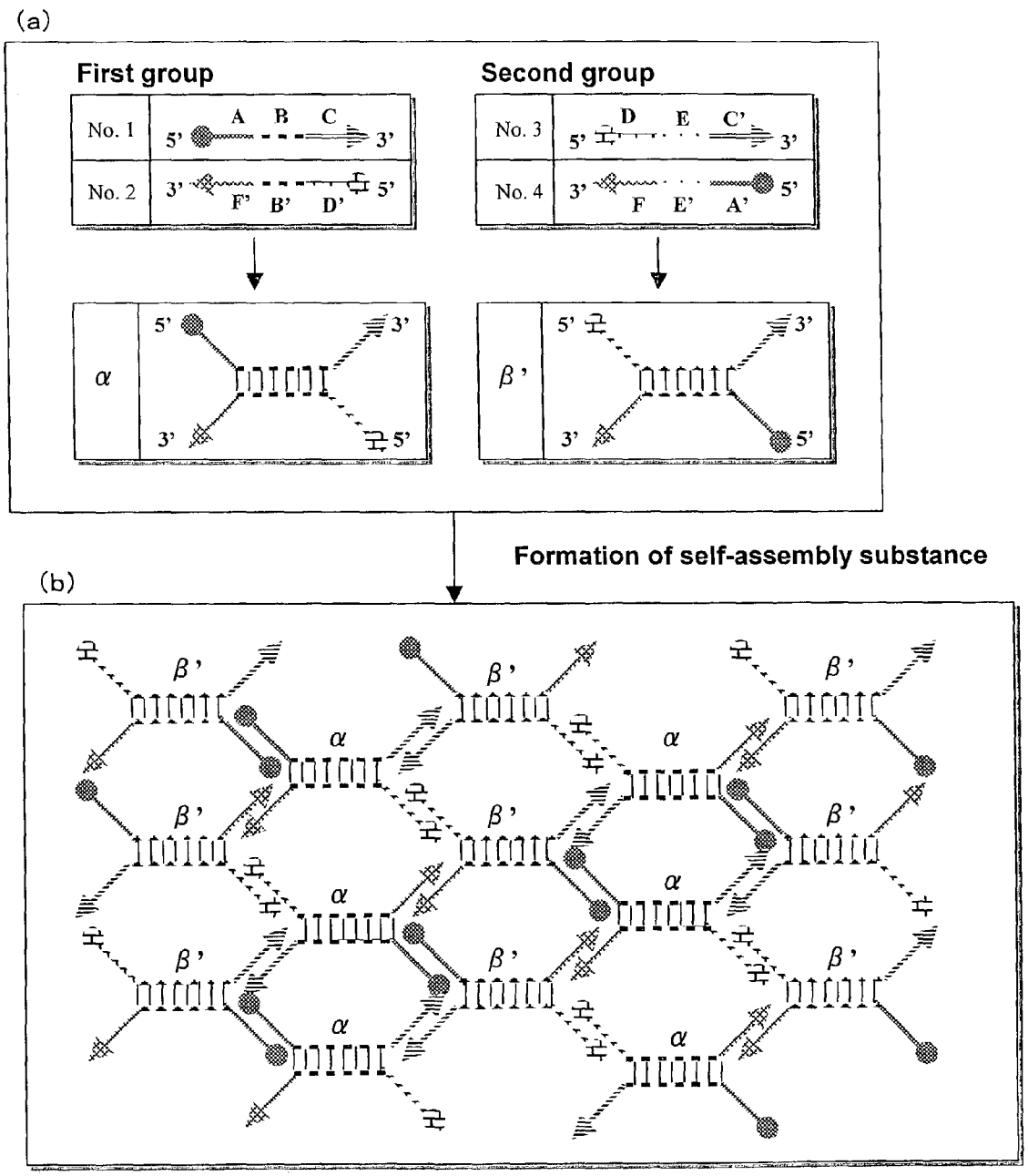
FIG. 4 is a schematic view showing an example of formation of a self-assembly substance with the two sets of dimer-probes shown in FIG. 3, and in this figure are shown the two sets of dimer-probes at (a), and a formed self-assembly substance at (b), respectively.

In the dimer-probe of the first group (α) and the dimer-probe of the second group (β'), as shown at (a) in FIG. 4, the 3' side region of the oligonucleotide No. 1 of the dimer-probe (α) and the 3' side region of the oligonucleotide No. 3 of the dimer-probe (β'), the 5' side region of the oligonucleotide No. 2 of the dimer-probe (α) and the 5' side region of the oligonucleotide No. 3 of the dimer-probe (β'), the 3' side region of the oligonucleotide No. 2 of the dimer-probe (α) and the 3' side region of the oligonucleotide No. 4 of the dimer-probe (β'), and the 5' side region of the oligonucleotide No. 1 of the dimer-probe (α) and the 5' side region of the oligonucleotide No. 4 of the dimer-probe (β') have base sequences complementary to each other, respectively. Thus by hybridizing the dimer-probes (α) and (β') to each other, the oligonucleotides are self-assembled to form a double-stranded self-assembly substance ((b) in FIG. 4).

3. The first example of formation of a self-assembly substance with n sets of dimer forming probes.

Plural groups are formed from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other.

In the dimer forming probes, (a) the 3' side region of the oligonucleotide No. 1 of the (n−1)th group and the 3' side region of the oligonucleotide No. 2 of the nth group, (b) the 5' side region of the oligonucleotide No. 2 of the (n−1)th group and the 5' side region of the oligonucleotide No. 1 of the nth group, (c) the 3' side region of the oligonucleotide No. 1 of the last group and the 3' side region of the oligonucleotide No. 2 of the first group, and (d) the 5' side region of the oligonucleotide No. 2 of the last group and the 5' side region of the oligonucleotide No. 1 of the first group have base sequences complementary to each other, respectively. Thus by hybridizing the dimer forming probes to each other, the oligonucleotides are self-assembled to form a double-stranded self-assembly substance.

Figure 5:
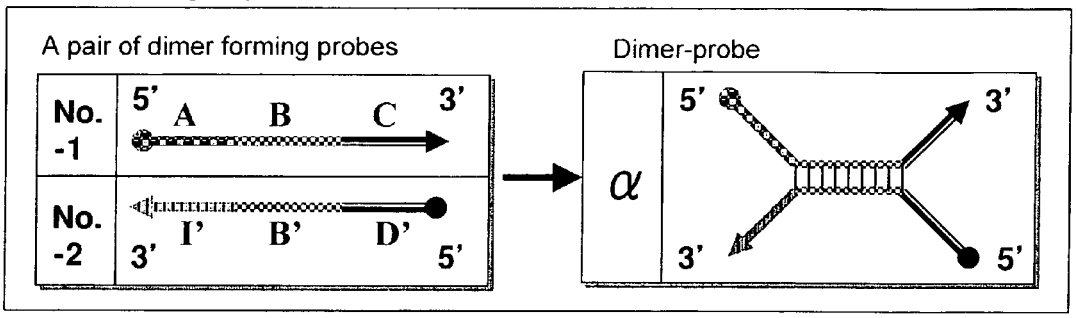
FIG. 5 is a schematic view showing an example of formation of three sets of dimer-probes in the method for forming the self-assembly substance according to the present invention, and in this figure are shown formation of a dimer-probe with a pair of dimer forming probes of a first group at (a), formation of a dimer-probe with a pair of dimer forming probes of a second group at (b), and formation of a dimer-probe with a pair of dimer forming probes of a third group at (c), respectively.
Figure 5:
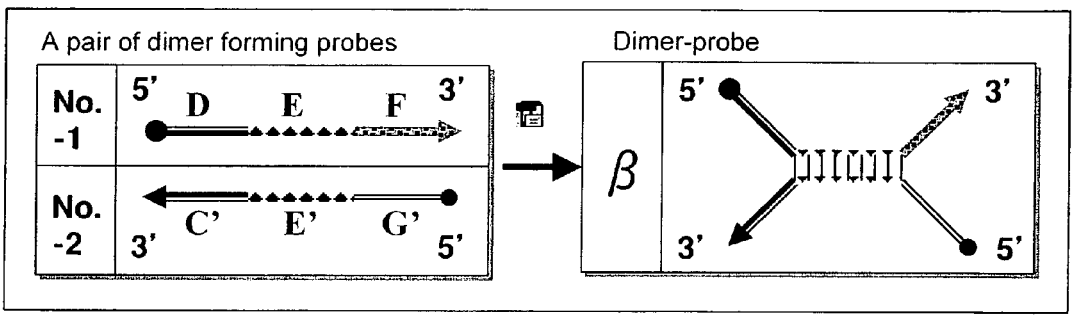
Figure 5:
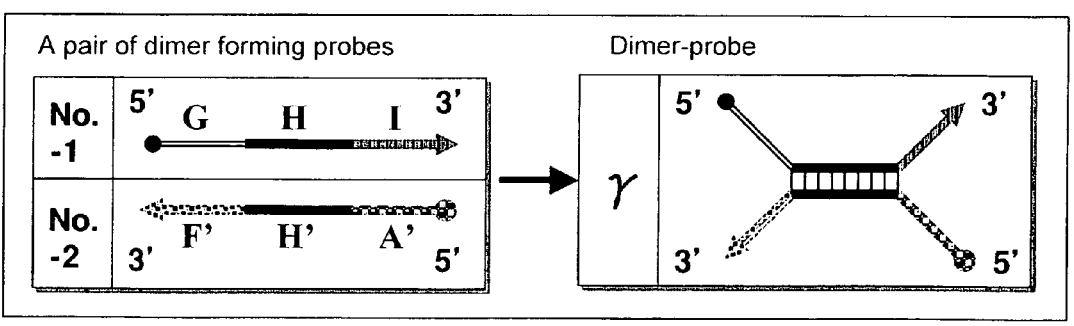
Figure 6:
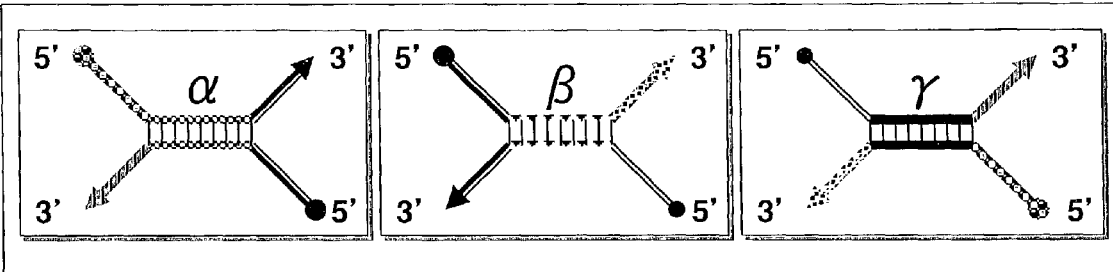
FIG. 6 is a schematic view showing an example of formation of a self-assembly substance with the three sets of dimer-probes shown in FIG. 5, and in this figure are shown the three sets of dimer-probes at (a), and a formed self-assembly substance at (b), respectively.
Figure 6:
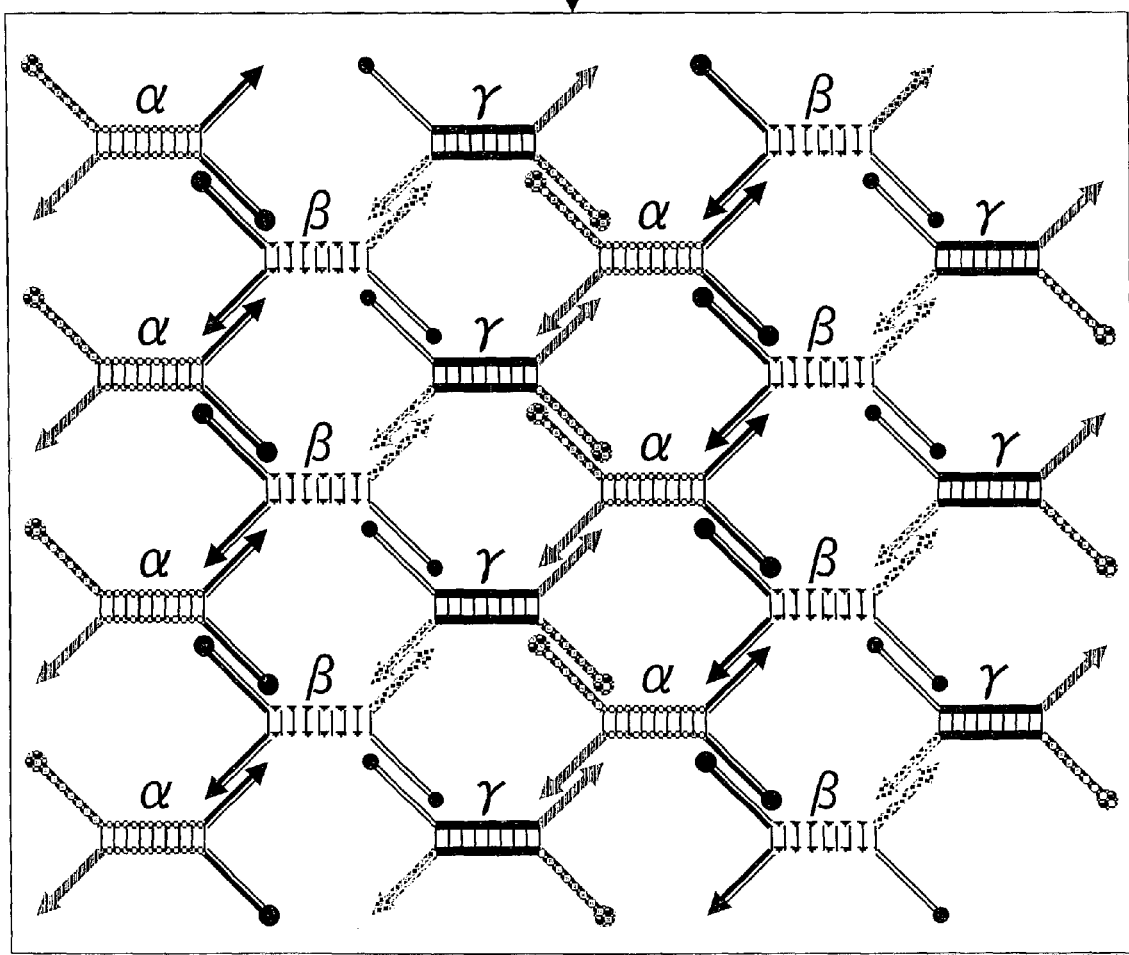
Figure 7:
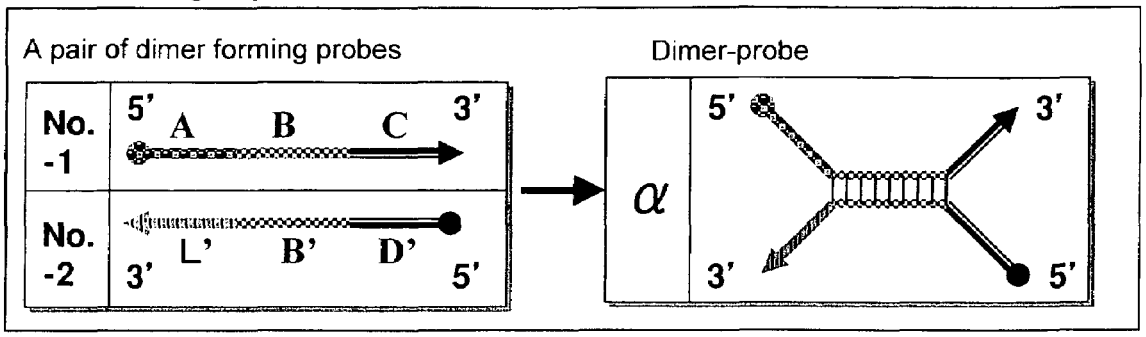
FIG. 7 is a schematic view showing an example of formation of four sets of dimer-probes in the method for forming the self-assembly substance according to the present invention, and in this figure are shown formation of a dimer-probe with a pair of dimer forming probes of a first group at (a), formation of a dimer-probe with a pair of dimer forming probes of a second group at (b), formation of a dimer-probe with a pair of dimer forming probes of a third group at (c), and formation of a dimer-probe with a pair of dimer forming probes of a fourth group at (d), respectively.
Figure 7:
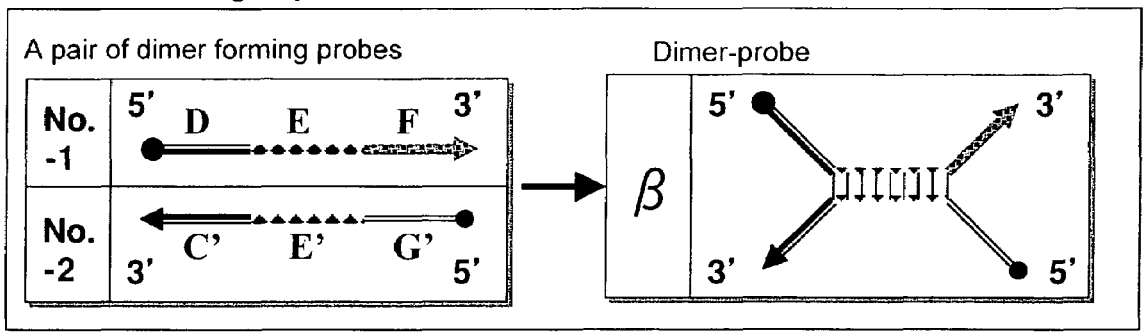
Figure 7:
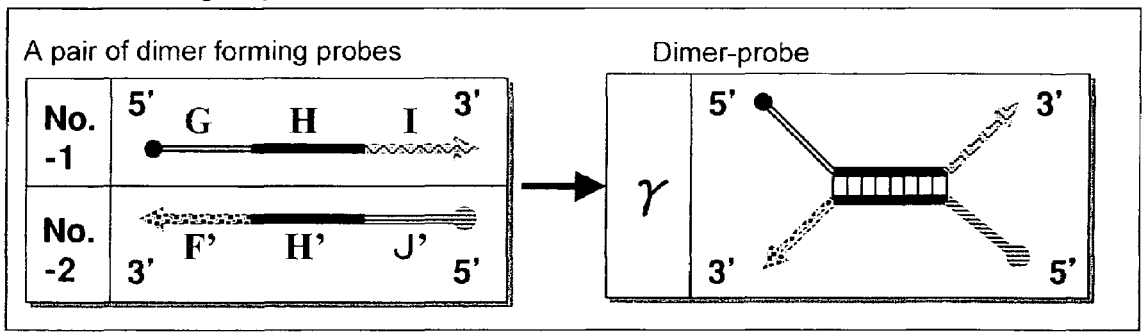
Figure 7:
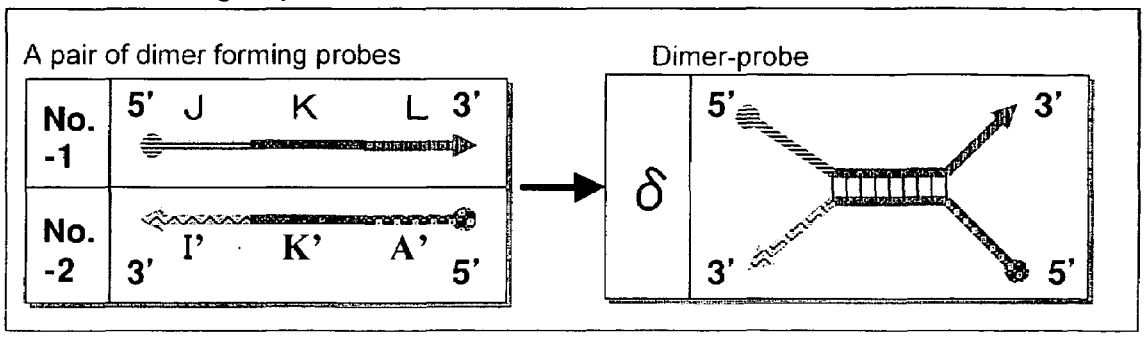
Figure 8:
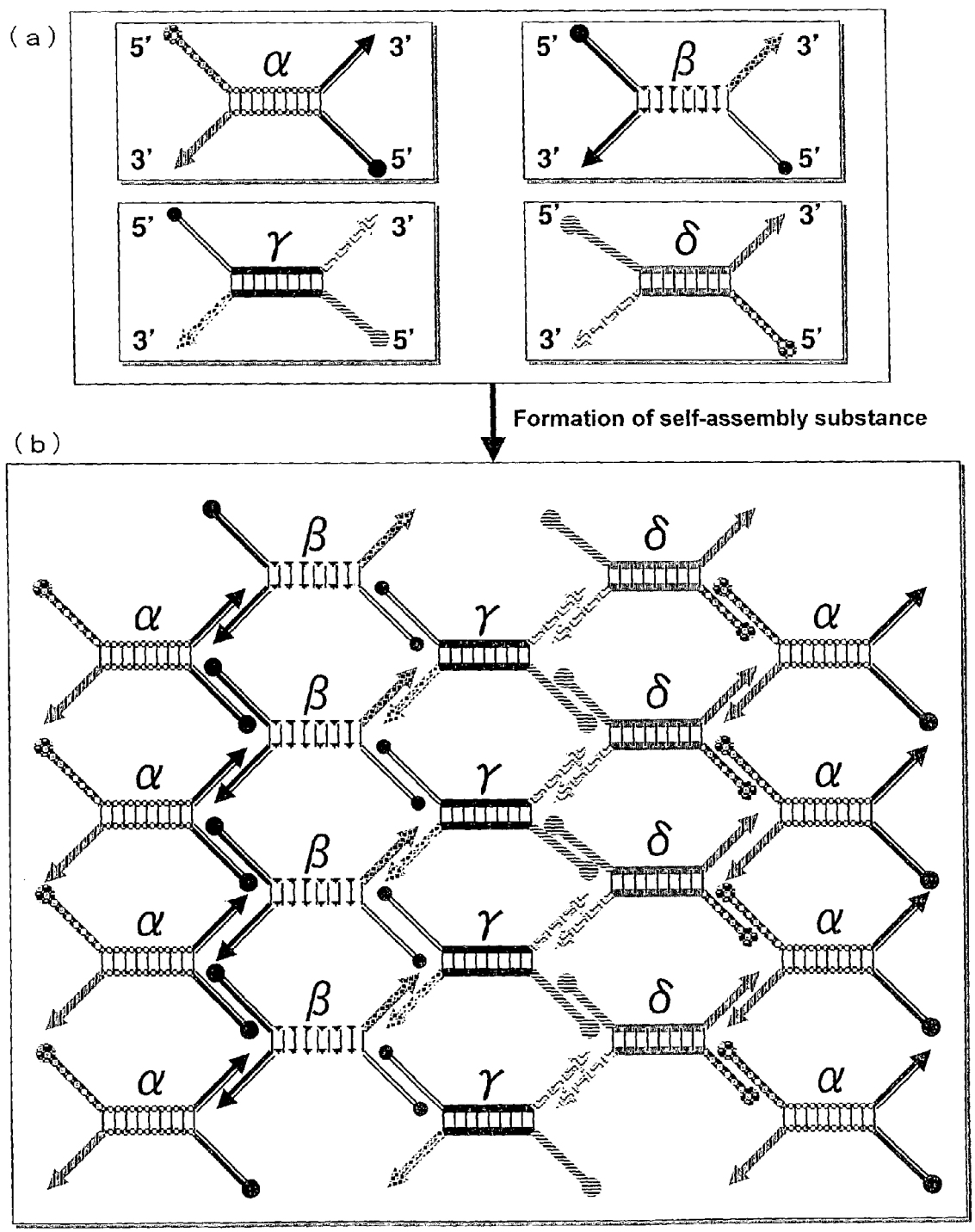
FIG. 8 is a schematic view showing an example of formation of a self-assembly substance with the four sets of dimer-probes shown in FIG. 7, and in this figure are shown the four sets of dimer-probes at (a), and a formed self-assembly substance at (b), respectively.

An example of n=3 in the above first example is shown in FIG. 5 and FIG. 6, and an example of n=4 in the above first example is shown in FIG. 7 and FIG. 8.

4. The first example of formation of a self-assembly substance with three sets of dimer forming probes.

As shown at (a) in FIG. 5, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β), and a pair of dimer forming probes of the third group and dimer-probes thereof (γ) have constitution as described above ((b) and (c) in FIG. 5).

In the dimer-probe of the first group (α), the dimer-probe of the second group (β) and the dimer-probe of the third group (γ), as shown in FIG. 5 and at (a) in FIG. 6, the 3' side region of the oligonucleotide No. 1 of the dimer-probe (α) and the 3' side region of the oligonucleotide No. 2 of the dimer-probe (β), the 5' side region of the oligonucleotide No. 2 of the dimer-probe (α) and the 5' side region of the oligonucleotide No. 1 of the dimer-probe (β), the 3' side region of the oligonucleotide No. 1 of the dimer-probe (β) and the 3' side region of the oligonucleotide No. 2 of the dimer-probe (γ), the 5' side region of the oligonucleotide No. 2 of the dimer-probe (β) and the 5' side region of the oligonucleotide No. 1 of the dimer-probe (γ), the 3' side region of the oligonucleotide No. 1 of the dimer-probe (γ) and the 3' side region of the oligonucleotide No. 2 of the dimer-probe (α), and the 5' side region of the oligonucleotide No. 2 of the dimer-probe (γ) and the 5' side region of the oligonucleotide No. 1 of the dimer-probe (α) have base sequences complementary to each other, respectively. Thus by hybridizing the dimer forming probes to each other, the oligonucleotides are self-assembled to form a double-stranded self-assembly substance ((b) in FIG. 6).

5. The first example of formation of a self-assembly substance with four sets of dimer forming probes.

As shown at (a) in FIG. 7, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β), a pair of dimer forming probes of the third group and dimer-probes thereof (γ), and a pair of dimer forming probes of the fourth group and dimer-probes thereof (δ) have constitution as described above ((b) to (d) in FIG. 7).

In the dimer-probe of the first group (α), the dimer-probe of the second group (β), the dimer-probe of the third group (γ) and the dimer-probe of the fourth group (δ), as shown in FIG. 7 and at (a) in FIG. 8, the 3' side region of the oligonucleotide No. 1 of the dimer-probe (α) and the 3' side region of the oligonucleotide No. 2 of the dimer-probe (β), the 5' side region of the oligonucleotide No. 2 of dimer-probe (α) and the 5' side region of the oligonucleotide No. 1 of the dimer-probe (β), the 3' side region of the oligonucleotide No. 1 of the dimer-probe (β) and the 3' side region of the oligonucleotide No. 2 of the dimer-probe (γ), the 5' side region of the oligonucleotide No. 2 of the dimer-probe (β) and the 5' side region of the oligonucleotide No. 1 of the dimer-probe (γ), the 3' side region of the oligonucleotide No. 1 of the dimer-probe (γ) and the 3' side region of the oligonucleotide No. 2 of the dimer-probe (δ), the 5' side region of the oligonucleotide No. 2 of the dimer-probe (γ) and the 5' side region of the oligonucleotide No. 1 of the dimer-probe (δ), the 3' side region of the oligonucleotide No. 1 of the dimer-probe (δ) and the 3' side region of the oligonucleotide No. 2 of the dimer-probe (α), and the 5' side region of the oligonucleotide No. 2 of the dimer-probe (δ) and the 5' side region of the oligonucleotide No. 1 of the dimer-probe (α) have base sequences complementary to each other, respectively. Thus by hybridizing the dimer forming probes to each other, the oligonucleotides are self-assembled to form a double-stranded self-assembly substance ((b) in FIG. 8).

6. The second example of formation of a self-assembly substance with n sets of dimer forming probes.

Plural groups are formed from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other.

In the dimer forming probes, (a) the 3' side region of the oligonucleotide No. 1 of the (n−1)th group and the 3' side region of the oligonucleotide No. 2 of the nth group, (b) the 5' side region of the oligonucleotide No. 1 of the (n−1)th group and the 5' side region of the oligonucleotide No. 2 of the nth group, (c) the 3' side region of the oligonucleotide No. 1 of the last group and the 3' side region of the oligonucleotide No. 2 of the first group, and (d) the 5' side region of the oligonucleotide No. 1 of the last group and the 5' side region of the oligonucleotide No. 2 of the first group have base sequences complementary to each other, respectively. Thus by hybridizing the dimer forming probes to each other, the oligonucleotides are self-assembled to form a double-stranded self-assembly substance.

Figure 9:
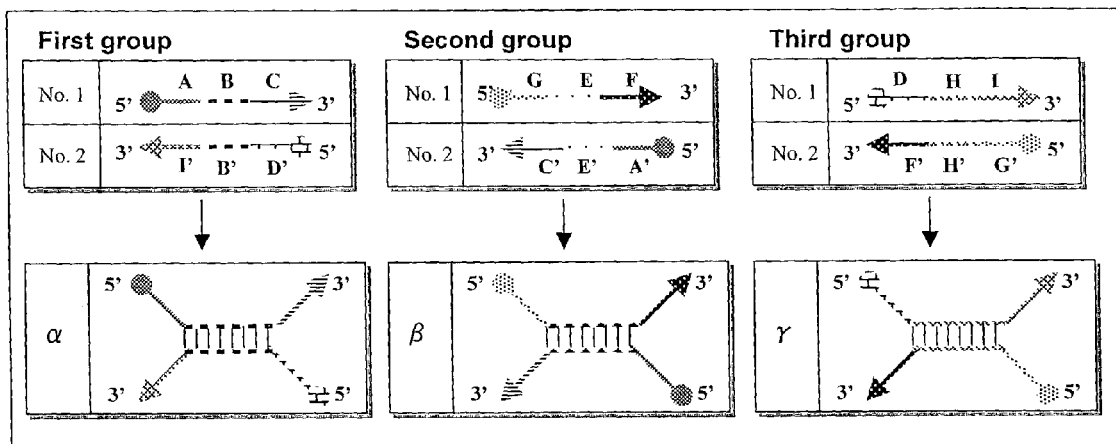
FIG. 9 is a schematic view showing another example of formation of three sets of dimer-probes in the method for forming the self-assembly substance according to the present invention, and in this figure are shown formation of a dimer-probe with a pair of dimer forming probes formed from a first group to a third group at (a), and a self-assembly substance formed with the three sets of dimer-probes at (b), respectively.
Figure 9:
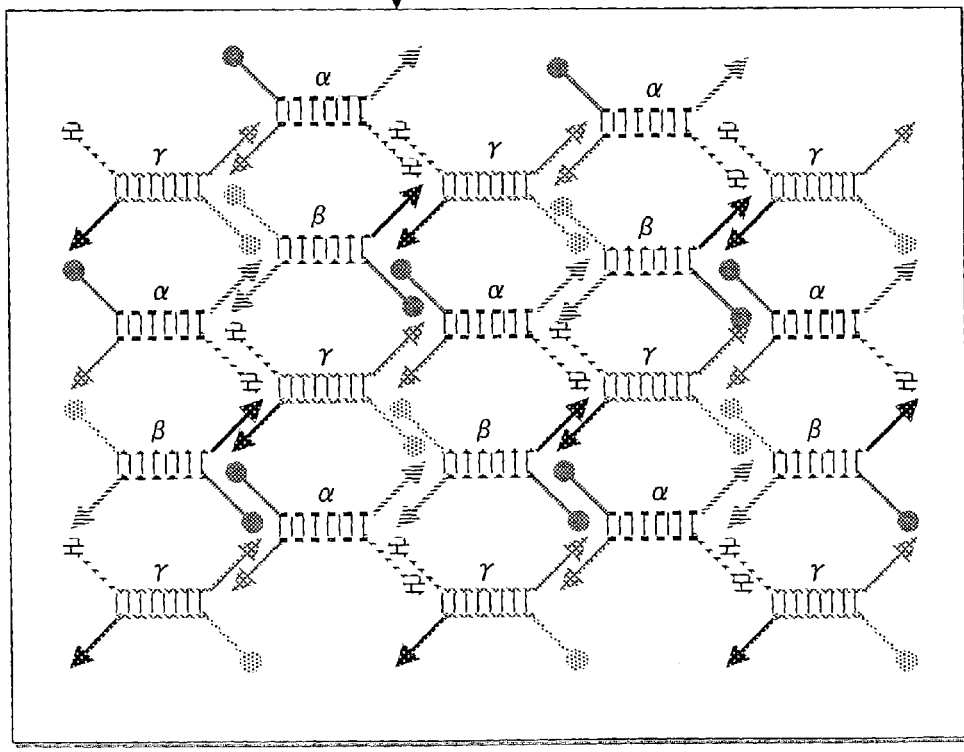
Figure 10:
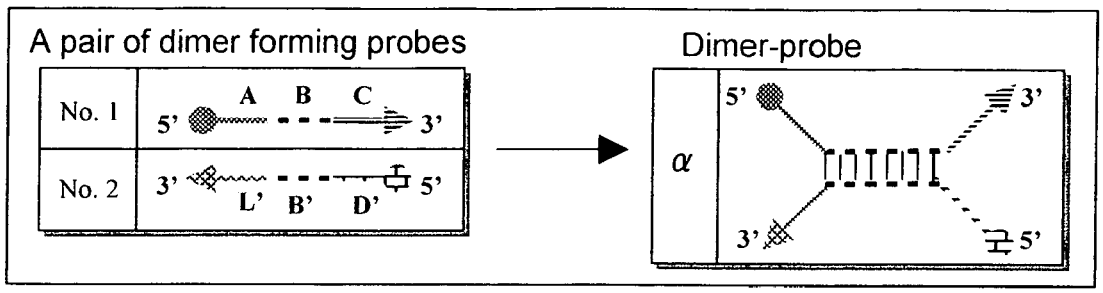
FIG. 10 is a schematic view showing another example of formation of four sets of dimer-probes in the method for forming the self-assembly substance according to the present invention, and in this figure are shown formation of a dimer-probe with a pair of dimer forming probes of a first group at (a), formation of a dimer-probe with a pair of dimer forming probes of a second group at (b), formation of a dimer-probe with a pair of dimer forming probes of a third group at (c), and formation of a dimer-probe with a pair of dimer forming probes of a fourth group at (d), respectively.
Figure 10:
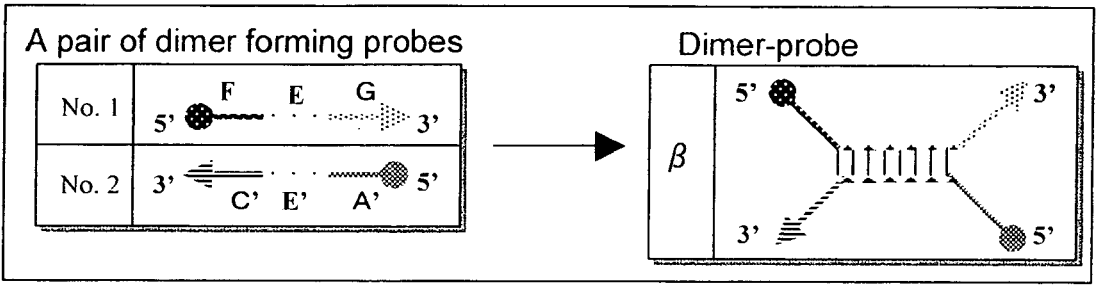
Figure 10:
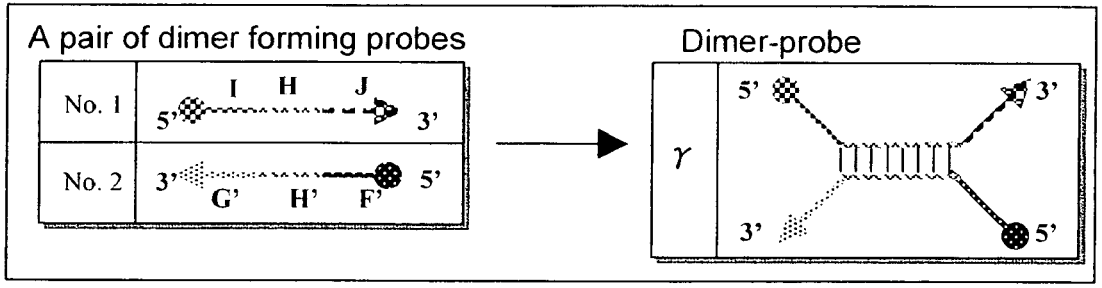
Figure 10:
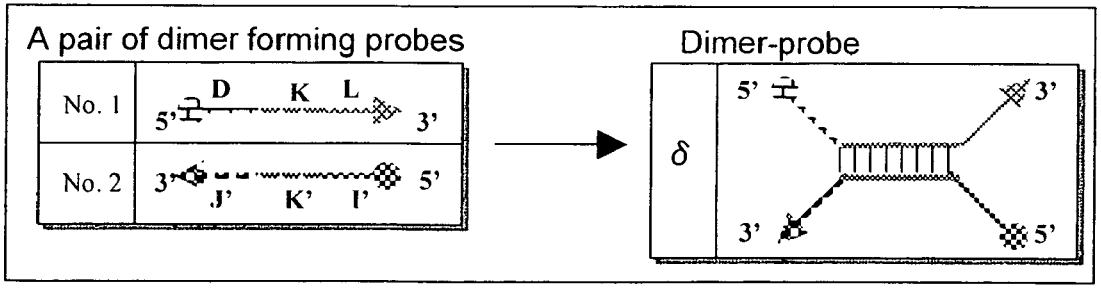
Figure 11:
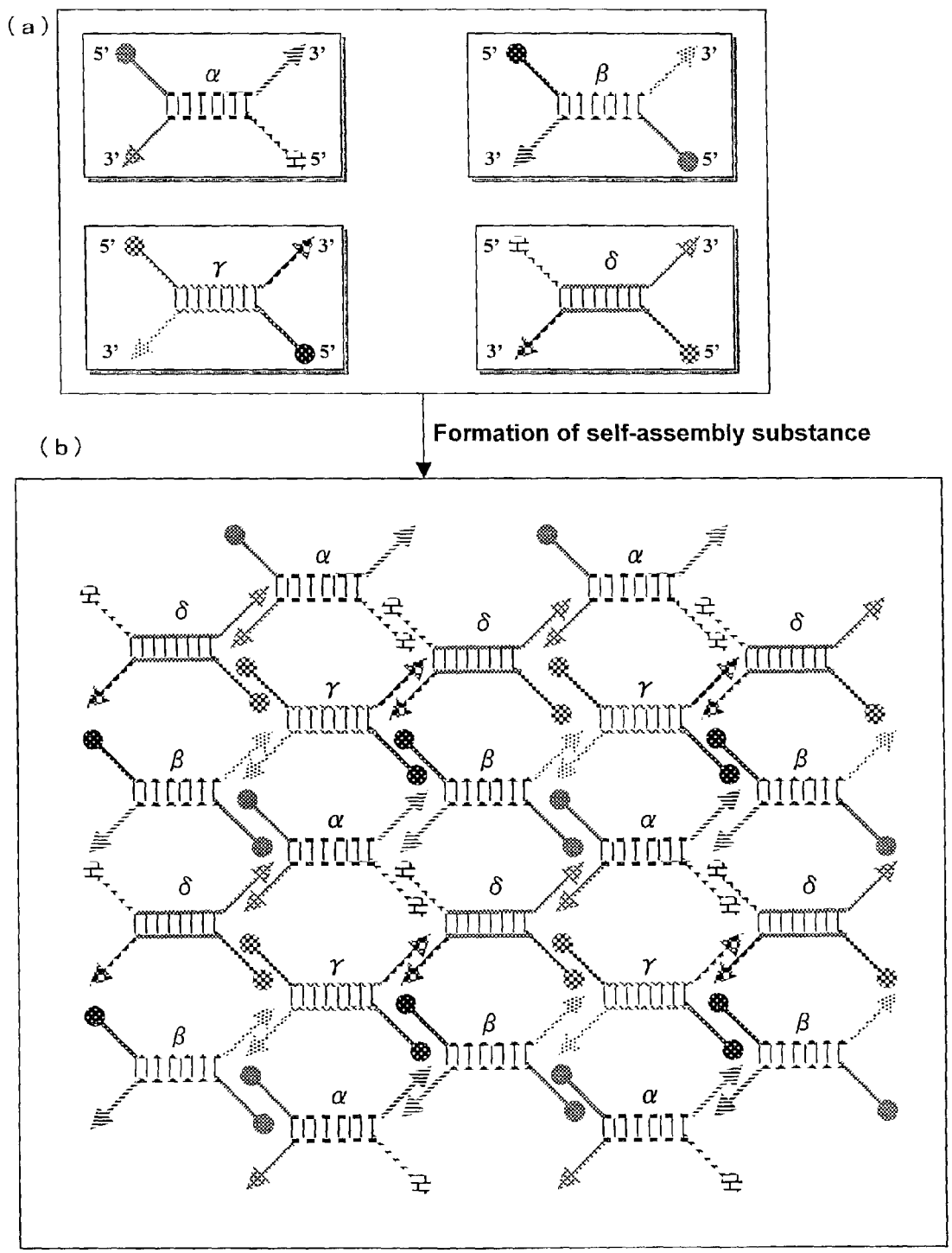
FIG. 11 is a schematic view showing an example of formation of a self-assembly substance with the four sets of dimer-probes shown in FIG. 10, and in this figure are shown the four sets of dimer-probes at (a), and a formed self-assembly substance at (b), respectively.
Figure 12:
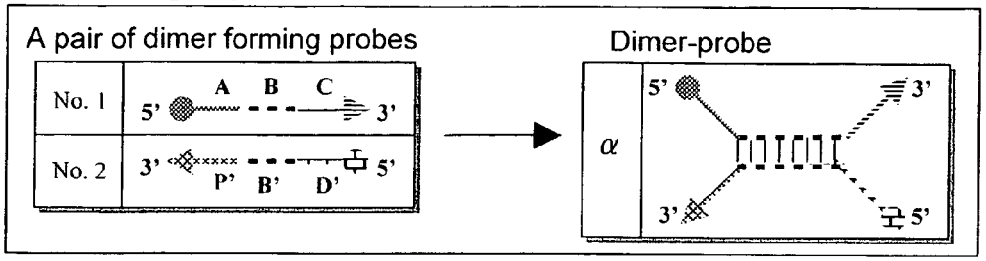
FIG. 12 is a schematic view showing an example of formation of five sets of dimer-probes in the method for forming the self-assembly substance according to the present invention, and in this figure are shown formation of a dimer-probe with a pair of dimer forming probes of a first group at (a), formation of a dimer-probe with a pair of dimer forming probes of a second group at (b), formation of a dimer-probe with a pair of dimer forming probes of a third group at (c), formation of a dimer-probe with a pair of dimer forming probes of a fourth group at (d), and formation of a dimer-probe with a pair of dimer forming probes of a fifth group at (e), respectively.
Figure 12:
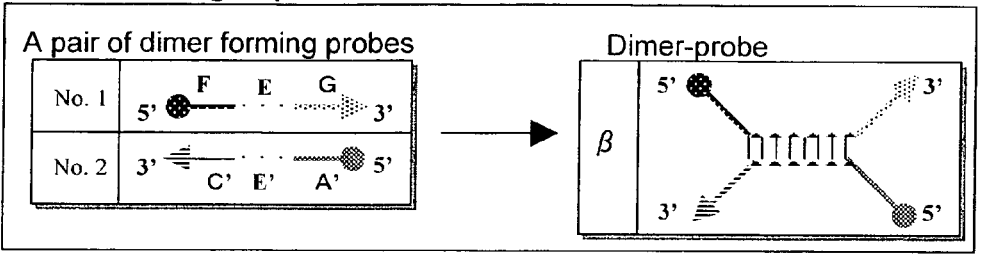
Figure 12:
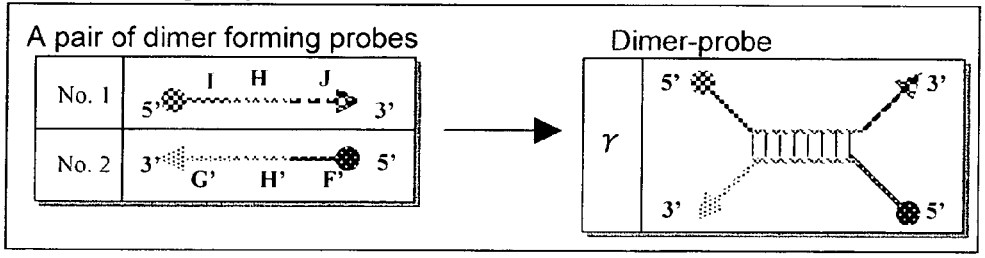
Figure 12:
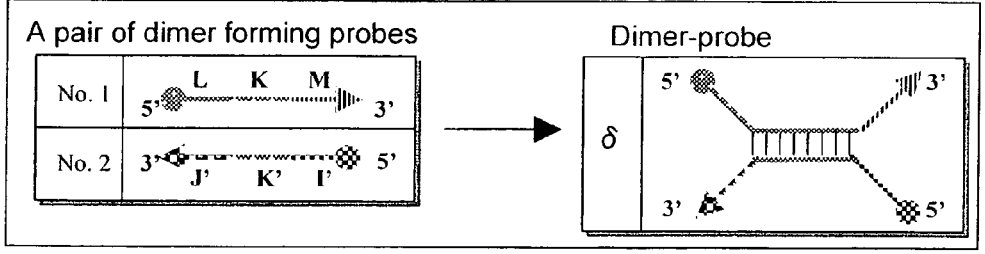
Figure 12:
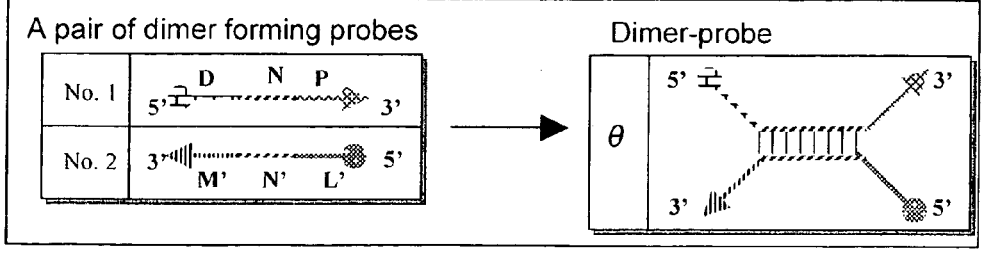
Figure 13:
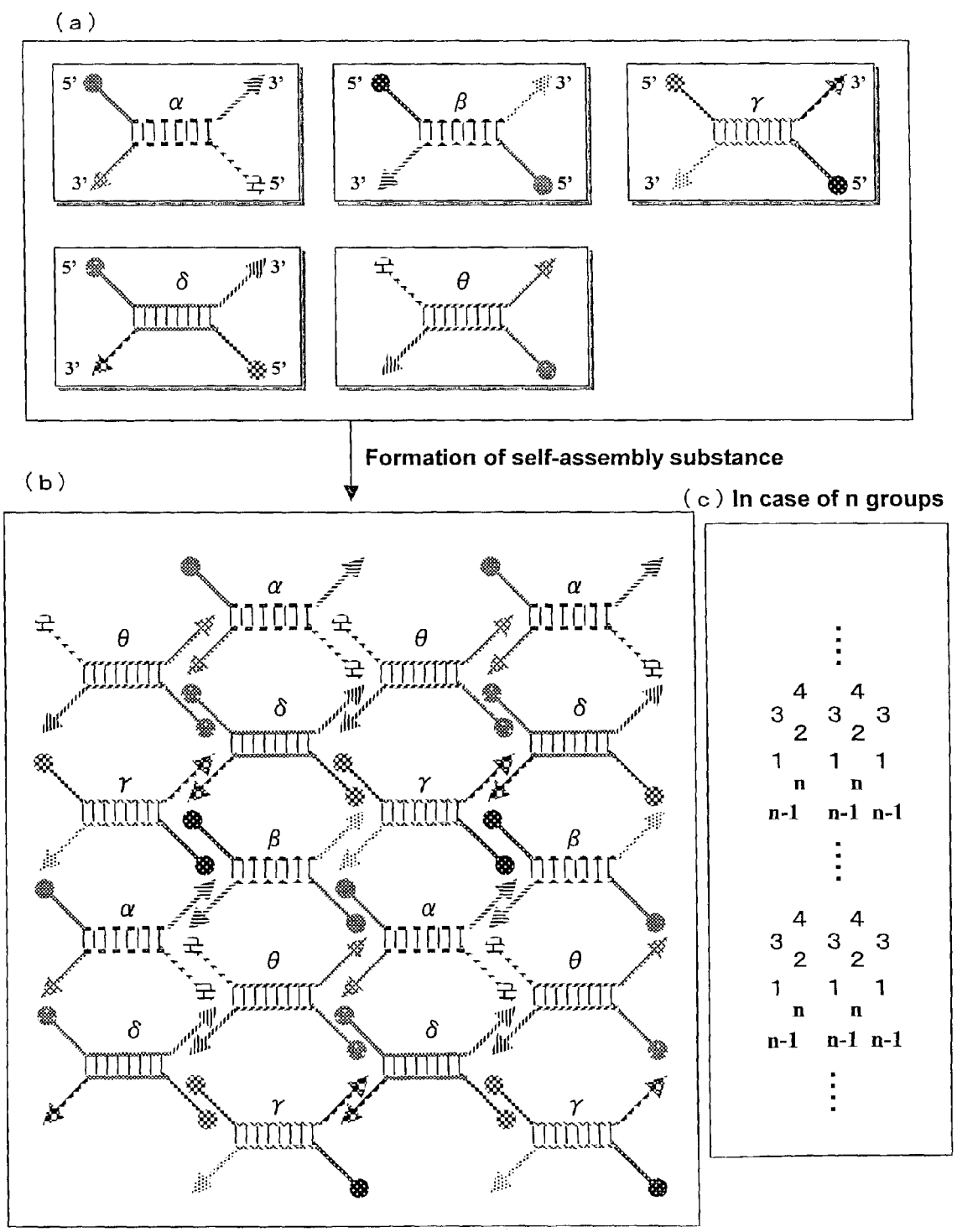
FIG. 13 is a schematic view showing an example of formation of a self-assembly substance with the five sets of dimer-probes shown in FIG. 12, and in this figure are shown the five sets of dimer-probes at (a), a formed self-assembly substance at (b), and an example of combinations of hybridization of n sets of dimer-probes in the case of n groups at (c), respectively.

An example of n=3 in the above second example is shown in FIG. 9, an example of n=4 in the above second example is shown in FIG. 10 and FIG. 11, and an example of n=5 in the above second example is shown in FIG. 12 and FIG. 13.

7. The second example of formation of a self-assembly substance with three sets of dimer forming probes.

As shown at (a) in FIG. 9, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β), and a pair of dimer forming probes of the third group and dimer-probes thereof (γ) have constitution as described above.

In the dimer-probe of the first group (α), the dimer-probe of the second group (β) and the dimer-probe of the third group (γ), as shown at (a) in FIG. 9, the 3' side region of the oligonucleotide No. 1 of the dimer-probe (α) and the 3' side region of the oligonucleotide No. 2 of the dimer-probe (β), the 5' side region of the oligonucleotide No. 1 of the dimer-probe (α) and the 5' side region of the oligonucleotide No. 2 of the dimer-probe (β), the 3' side region of the oligonucleotide No. 1 of the dimer-probe (β) and the 3' side region of the oligonucleotide No. 2 of the dimer-probe (γ), the 5' side region of the oligonucleotide No. 1 of the dimer-probe (β) and the 5' side region of the oligonucleotide No. 2 of the dimer-probe (γ), the 3' side region of the oligonucleotide No. 1 of the dimer-probe (γ) and the 3' side region of the oligonucleotide No. 2 of the dimer-probe (α), and the 5' side region of the oligonucleotide No. 1 of the dimer-probe (γ) and the 5' side region of the oligonucleotide No. 2 of the dimer-probe (α) have base sequences complementary to each other, respectively. Thus by hybridizing the dimer forming probes to each other, the oligonucleotides are self-assembled to form a double-stranded self-assembly substance ((b) in FIG. 9).

8. The second example of formation of a self-assembly substance with four sets of dimer forming probes.

As shown at (a) in FIG. 10, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β), a pair of dimer forming probes of the third group and dimer-probes thereof (γ), and a pair of dimer forming probes of the fourth group and dimer-probes thereof (δ) have constitution as described above ((b) to (d) in FIG. 10).

In the dimer-probe of the first group (α), the dimer-probe of the second group (β), the dimer-probe of the third group (γ) and the dimer-probe of the fourth group (δ), as shown in FIG. 10 and at (a) in FIG. 11, the 3' side region of the oligonucleotide No. 1 of the dimer-probe (α) and the 3' side region of the oligonucleotide No. 2 of the dimer-probe (β), the 5' side region of the oligonucleotide No. 1 of the dimer-probe (α) and the 5' side region of the oligonucleotide No. 2 of the dimer-probe (β), the 3' side region of the oligonucleotide No. 1 of the dimer-probe (β) and the 3' side region of the oligonucleotide No. 2 of the dimer-probe (γ), the 5' side region of the oligonucleotide No. 1 of the dimer-probe (β) and the 5' side region of the oligonucleotide No. 2 of the dimer-probe (γ), the 3' side region of the oligonucleotide No. 1 of the dimer-probe (γ) and the 3' side region of the oligonucleotide No. 2 of the dimer-probe (δ), the 5' side region of the oligonucleotide No. 1 of the dimer-probe (γ) and the 5' side region of the oligonucleotide No. 2 of the dimer-probe (δ), the 3' side region of the oligonucleotide No. 1 of the dimer-probe (δ) and the 3' side region of the oligonucleotide No. 2 of the dimer-probe (α), and the 5' side region of the oligonucleotide No. 1 of the dimer-probe (δ) and the 5' side region of the oligonucleotide No. 2 of the dimer-probe (α) have base sequences complementary to each other, respectively. Thus by hybridizing the dimer forming probes to each other, the oligonucleotides are self-assembled to form a double-stranded self-assembly substance ((b) in FIG. 11).

9. The second example of formation of a self-assembly substance with five sets of dimer forming probes.

As shown at (a) in FIG. 12, the first group includes a pair of dimer forming probes containing a pair of oligonucleotides No. 1 and No. 2, each oligonucleotide having three regions of a 3' side region, a mid-region and a 5' side region, in which the mid-regions of the oligonucleotides have complementary to each other, thereby forming dimer-probes of the first group (α) with the 3' side regions and the 5' side regions having not complementary to each other. Similarly, a pair of dimer forming probes of the second group and dimer-probes thereof (β), a pair of dimer forming probes of the third group and dimer-probes thereof (γ), a pair of dimer forming probes of the fourth group and dimer-probes thereof (δ), and a pair of dimer forming probes of the fifth group and dimer-probes thereof (θ) have constitution as described above ((b) to (d) in FIG. 12).

In the dimer-probe of the first group (α), the dimer-probe of the second group (β), the dimer-probe of the third group (γ), the dimer-probe of the fourth group (δ) and the dimer-probe of the fifth group (θ), as shown in FIG. 12 and at (a) in FIG. 13, the 3' side region of the oligonucleotide No. 1 of the dimer-probe (α) and the 3' side region of the oligonucleotide No. 2 of the dimer-probe (β), the 5' side region of the oligonucleotide No. 1 of the dimer-probe (α) and the 5' side region of the oligonucleotide No. 2 of the dimer-probe (β), the 3' side region of the oligonucleotide No. 1 of the dimer-probe (β) and the 3' side region of the oligonucleotide No. 2 of the dimer-probe (γ), the 5' side region of the oligonucleotide No. 1 of the dimer-probe (β) and the 5' side region of the oligonucleotide No. 2 of the dimer-probe (γ), the 3' side region of the oligonucleotide No. 1 of the dimer-probe (γ) and the 3' side region of the oligonucleotide No. 2 of the dimer-probe (δ), the 5' side region of the oligonucleotide No. 1 of the dimer-probe (γ) and the 5' side region of the oligonucleotide No. 2 of the dimer-probe (δ), the 3' side region of the oligonucleotide No. 1 of the dimer-probe (δ) and the 3' side region of the oligonucleotide No. 2 of the dimer-probe (θ), the 5' side region of the oligonucleotide No. 1 of the dimer-probe (δ) and the 5' side region of the oligonucleotide No. 2 of the dimer-probe (θ), the 3' side region of the oligonucleotide No. 1 of the dimer-probe (θ) and the 3' side region of the oligonucleotide No. 2 of the dimer-probe (α), and the 5' side region of the oligonucleotide No. 1 of the dimer-probe (θ) and the 5' side region of the oligonucleotide No. 2 of the dimer-probe (α) have base sequences complementary to each other, respectively. Thus by hybridizing the dimer forming probes to each other, the oligonucleotides are self-assembled to form a double-stranded self-assembly substance ((b) in FIG. 13).

Furthermore, in the above second example, as an example of formation of a self-assembly substance with n sets of dimer forming probes included in n groups, a self-assembly substance is formed by hybridizing n sets of dimer-probes with the combination as shown in (c) in FIG. 13.

As a preferable method for hybridizing the dimer forming probes, the method for forming the self-assembly substance by previously hybridizing the dimer forming probes to form the dimer-probes, and then hybridizing the dimer-probes formed for each group was described above. However the method for forming the self-assembly substance according to the present invention is not limited to the method described above, and contains, for example, the method in which the self-assembly substance is formed by reacting the dimer forming probes of each group all at once to hybridize the probes.

Furthermore, the present invention provides the method in which at least one G (guanine) or C (cytosine) is arranged at one or more ends of the three regions of the dimer forming probes, and in hybridizing the dimer forming probes, at least one G—C bond is formed at the ends of the regions, thus the special interaction by π electrons of bases attributable to the stacking of bases being generated to form a stable double-stranded self-assembly substance.

In the method for forming the self-assembly substance, the inventors have worked out that when the bond strength at branched sites of each region is weak, the hybridization of the region sandwiched by the branched sites is unstabilized; therefore, the effect of the stacking of bases resulting from the special interaction by π electrons of bases in the whole of the region is increased so as to strengthen the hybridization reaction at each region.

The number of C or G arranged at the ends of the regions may be at least one base, a plurality of bases being applicable. In consideration of the base sequence of each region, the number of such bases can be suitably selected. If two or more C and G are to be arranged, C and G can be combined arbitrarily and arranged in any order.

In the present invention, the stacking of bases in the self-assembly substance formed according to the present invention has a regular higher-order structure bringing about a hypochromic effect called "hypochromism" reducing the intensity of an absorption band at 260 nm in the ultraviolet region, whereby the state of the self-assembly substance can be confirmed.

Furthermore, in the present invention, by adding a fluorescent substance having the property of bonding to a nucleic acid to base pairs of the self-assembly substance and checking a change in fluorescence intensity, the state of the self-assembly substance can be confirmed. For example, the self-assembly substance can be detected by adding a coloring matter that is inserted into two strands of oligonucleotides to emit fluorescence, and monitoring emission of fluorescence with the I-CORE™ (Smart Cycler™) made by Cepheid Inc., and so forth.

The formed self-assembly substance can easily be also detected by the general agarose gel electrophoresis.

EXAMPLES

Hereinafter, the present invention is described in more detail by reference to Examples, but it is needless to say that the present invention is not limited to the Examples.

Oligonucleotide probes used in the Examples.

```
    1) Probe No. 1              (SEQ ID NO:1)
5'-GTGCTGACTT AACCGGATAC GAACAGGATC CTAGACCTAG  CAT
AGTACAG TCCGATGGTG-3'

2) Probe No. 2              (SEQ ID NO:2)
5'-CCTCAAGACG CATGTCTTTC CTAGGTCTAG GATCCTGTTC  CTA
GAACGGA CTGTACTTCG-3'

3) Probe No. 3              (SEQ ID NO:3)
5'-GAAAGACATG CGTCTTGAGG CTATCCGTTC GACTTGCATG  CGA
AGTACAG TCCGTTCTAG-3'

4) Probe No. 4              (SEQ ID NO:4)
5'-GTATCCGGTT AAGTCAGCAC CATGCAAGTC GAACGGATAG  CAC
CATCGGA CTGTACTATG-3'

5) Probe X1                 (SEQ ID NO:5)
5'-GTGCTGACTT AACCGGATAC GAACAGGATC CTAGACCTAG  CAT
AGTACAG TCCGATGGTG-3'

6) Probe X2                 (SEQ ID NO:6)
5'-CCTCAAGACG CATGTCTTTC CTAGGTCTAG GATCCTGTTC  CTA
GAACGGA CTGTACTTCG-3'

7) Probe Y1                 (SEQ ID NO:7)
5'-GAAAGACATG CGTCTTGAGG CTATCCGTTC GACTTGCATG  CTA
GACGCTT CTTGCGTAAG-3'
```

-continued

```
    8) Probe Y2                 (SEQ ID NO:8)
5'-GTGTCGAATT GACACTCAGC CATGCAAGTC GAACGGATAG  CAC
CATCGGA CTGTACTATG-3'

9) Probe Z1                 (SEQ ID NO:9)
5'-GCTGAGTGTC AATTCGACAC GCACCCTATC AGGCAGTATC  CGA
AGTACAG TCCGTTCTAG-3'

10) Probe Z2                (SEQ ID NO:10)
5'-GTATCCGGTT AAGTCAGCAC GATACTGCCT GATAGGGTGC  CTT
ACGCAAG AAGCGTCTAG-3'
```

Experimental Examples 1 to 6

1. Object

Formation of dimer-probes with two sets of pairs of dimer forming probes of the first and second groups was proved.

2. Materials (1) The probes No. 1 and No. 2 were prepared as a pair of dimer forming probes of the first group, and the probes No. 3 and No. 4 were prepared as a pair of dimer forming probes of the second group. The oligonucleotide probes each prepared to the concentration of 100 pmol were used.

(2) 20×SSC (3M-NaCl, 0.3M-$C_6H_5O_7Na_3$·$2H_2O$, pH 7) was used as a buffer solution.

3. Method

Experimental Examples 1 to 4

Preparation of Dimer Forming Probes

1 μL of oligonucleotide probe, 12 μL of 20×SSC and 7 μL of $H_2O$ were added to 0.2 mL microtubes each to obtain 20 μL of reaction solution. As the oligonucleotide probes, the probe No. 1 was used in Experimental example 1, the probe No. 2 in Experimental example 2, the probe No. 3 in Experimental example 3, and the probe No. 4 in Experimental example 4, respectively.

Each of the reaction solutions was heated for 30 seconds at 94° C.

After completion of the reaction, the reaction solutions were rapidly cooled on ice, and were subjected to electrophoresis using 0.5% agarose gel for 30 minutes at 100 V. After completion of the agarose gel electrophoresis, the gel was stained with ethidium bromide.

Experimental Examples 5 and 6

Preparation of Dimer-probes

In Experimental example 5, 0.5 μL of probe No. 1, 0.5 μL of probe No. 2, 12 μL of 20×SSC and 7 μL of $H_2O$ were added to a 0.2 mL microtube to obtain 20 μL of reaction solution.

In Experimental example 6, 0.5 μL of probe No. 3, 0.5 μL of probe No. 4, 12 μL of 20×SSC and 7 μL of $H_2O$ were added to a 0.2 mL microtube to obtain 20 μL of reaction solution.

Each of the reaction solutions was heated for 30 seconds at 94° C., and then was reacted for 30 minutes at 64° C.

After completion of the reaction, the reaction solutions were rapidly cooled on ice, and were subjected to electrophoresis for 30 minutes at 100 V using 0.5% agarose gel. After completion of the agarose gel electrophoresis, the gel was stained with ethidium bromide.

4. Result

Figure 17:
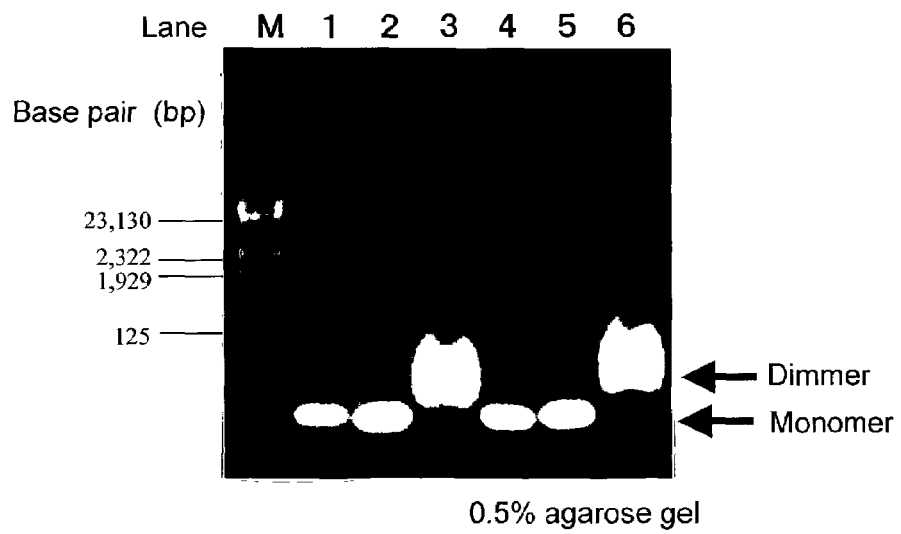
FIG. 17 is a photograph showing results of Experimental examples 1 to 4 (lanes 1, 2, 4 and 5) and Experimental examples 5 and 6 (lanes 3 and 6).
Figure 17:
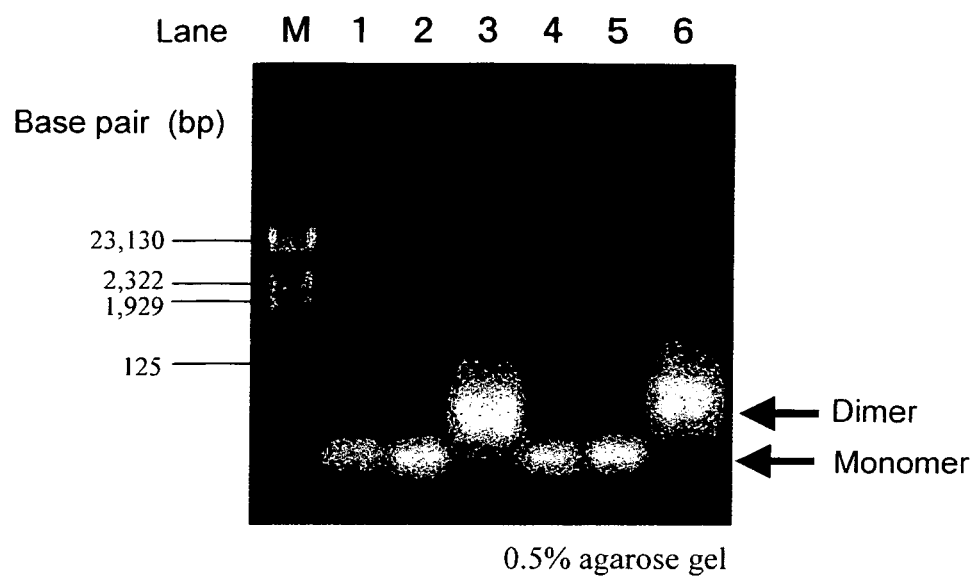

The result is shown in FIG. 17. As shown in a photograph of agarose gel electrophoresis of FIG. 17, in Experimental examples 1 to 4, it was confirmed that each dimer forming probe was in the state of monomer (lane 1, 2, 4 and 5). In Experimental example 5, as shown in the photograph of agarose gel electrophoresis of FIG. 17, different from oligonucleotide probes used by the PALSAR method, a pair of dimer forming probes of the first group according to the present invention were oligonucleotide probes which did not form a self-assembly substance and formed only a dimer (lane 3). Similarly, in Experimental example 6, different from the oligonucleotide probe used by the PALSAR method, a pair of dimer forming probes of the second group according to the present invention did not form a self-assembly substance, and formed only a dimer (lane 6).

Inventive Example 1

1. Object

Two sets of dimer-probes were formed previously, and formation of a self-assembly substance was proved.

2. Materials (1) The dimer of the first group formed in Experimental example 5 was used as a dimer-probe of the first group (α) and the dimer of the second group formed in Experimental example 6 was used as a dimer-probe of the second group (β).

(2) 20×SSC (3M-NaCl, 0.3M-$C_6H_5O_7Na_3 \cdot 2H_2O$, pH 7) was used as a buffer solution.

3. Method 0.5 µL of dimer-probe (α) of the first group, 0.5 µL of dimer-probe (β) of the second group, 12 µL of 20×SSC, and 7 µL of $H_2O$ were added to 0.2 mL microtubes each to obtain 20 µL of reaction solutions.

The reaction solutions were for 30 minutes at 52° C., 54° C., 56° C., 58° C., 60° C., 62° C., 64° C., 66° C., 68° C. and 70° C., respectively.

After completion of the reaction, the reaction solutions were rapidly cooled on ice, and were subjected to electrophoresis for 30 minutes at 100 V using 0.5% agarose gel. After completion of the agarose gel electrophoresis, the gel was stained with ethidium bromide.

4. Result

Figure 14:
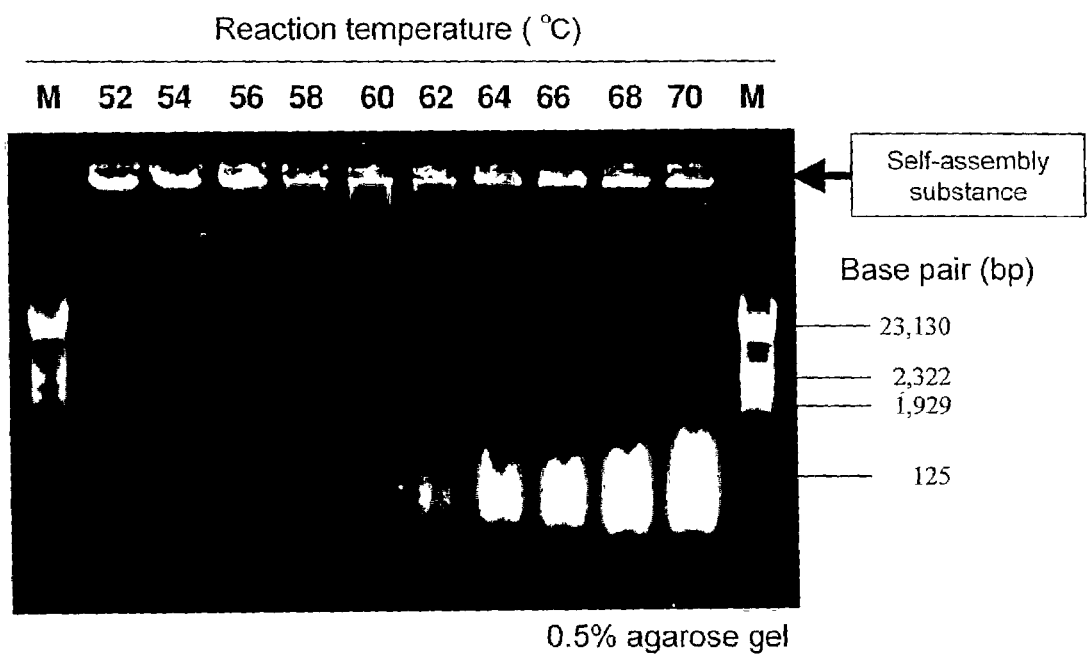
FIG. 14 is a photograph showing result of Inventive example 1.

As shown in a photograph of FIG. 14, by comparison with the PALSAR method, formation of the self-assembly substance was confirmed in a wide temperature range although the same reaction time. This is expected to shorten reaction time.

Inventive Example 2

1. Object

Four types of dimer forming probes were reacted all at once, and formation of a self-assembly substance was proved.

2. Materials (1) The probes No. 1 and No. 2 were used as dimer forming probes of the first group, and the probes No. 3 and No. 4 were used as dimer forming probes of the second group. Those prepared in Experimental examples 1 to 4 were used for each of the oligonucleotide probes.

(2) 20×SSC (3M-NaCl, 0.3M-$C_6H_5O_7Na_3 \cdot 2H_2O$, pH 7.) was used as a buffer solution.

3. Method 0.5 µL of each of the probes No. 1, No. 2, No. 3 and No. 4 were simultaneously added to 0.2 mL microtubes each, and 12 µL of 20×SSC and 6 µL of $H_2O$ further added thereto to obtain 20 µL of reaction solutions.

The reaction solutions were for 30 minutes at 52° C., 54° C., 56° C., 58° C., 60° C., 62° C., 64° C., 66° C., 68° C. and 70° C., respectively.

After completion of the reaction, the reaction solutions were rapidly cooled on ice, and were subjected to electrophoresis for 30 minutes at 100 V using 0.5% agarose gel. After completion of the agarose gel electrophoresis, the gel was stained with ethidium bromide.

4. Result

Figure 15:
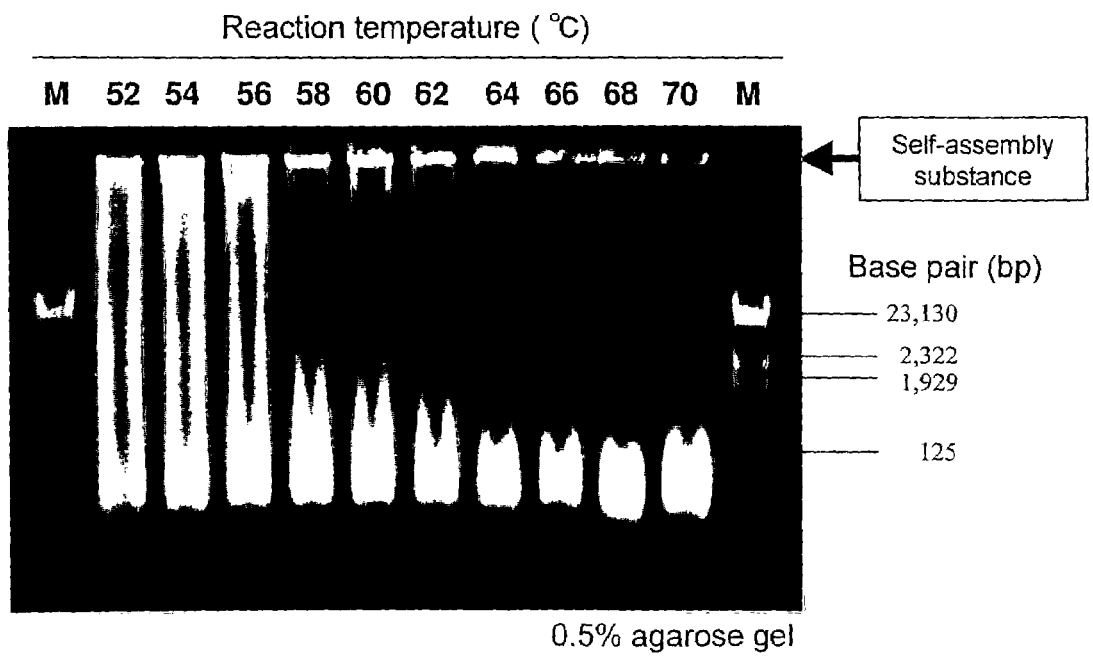
FIG. 15 is a photograph showing result of Inventive example 2.

As shown in a photograph of FIG. 15, formation of a self-assembly substance was observed, by comparison with Inventive example 1, non-specific reaction was observed under the reaction temperature in the range from 52° C. to 62° C.

Inventive Example 3

1. Object

Formation of a self-assembly substance was examined by using three sets of pairs of dimer forming probes of the first, second and third groups. In Inventive example 1 and Inventive example 2, even when the probes were previously prepared to the dimer, and when the probes were simultaneously added, formation of the self-assembly substance was confirmed under the same reaction temperature, and therefore in this Inventive example, the types of dimers for probe increase to three sets, and the probes were simultaneously added to check formation of a self-assembly substance under the same reaction temperature.

2. Materials (1) The probes X1 and X2 were used as dimer forming probes of the first group, and also the probes Y1 and Y2 as dimer forming probes of the second group, and the probes Z1 and Z2 as dimer forming probes of the third group. The oligonucleotide probes each prepared to the concentration of 100 pmol were used.

(2) 20×SSC (3M-NaCl, 0.3M-$C_6H_5O_7Na_3 \cdot 2H_2O$, pH 7) was used as a buffer solution.

3. Method 0.5 µL of each of the probes X1, X2, Y1, Y2, Z1 and Z2 were added to 0.2 mL microtubes each all at once, and 18 µL of 20×SSC and 9 µL of $H_2O$ further added thereto to obtain 30 µL of reaction solutions.

Each of the reaction solutions was heated for 30 seconds at 94° C.

After the warning, the reaction solutions were for 30 minutes at 52° C., 54° C., 56° C., 58° C., 60° C., 62° C., 64° C., 66° C., 68° C., 70° C., 72° C., and 74° C., respectively.

After completion of the reaction, the reaction solutions were rapidly cooled on ice, and were subjected to electrophoresis for 30 minutes at 100 V using 0.5% agarose gel. After completion of the agarose gel electrophoresis, the gel was stained with ethidium bromide.

4. Result

Figure 16:
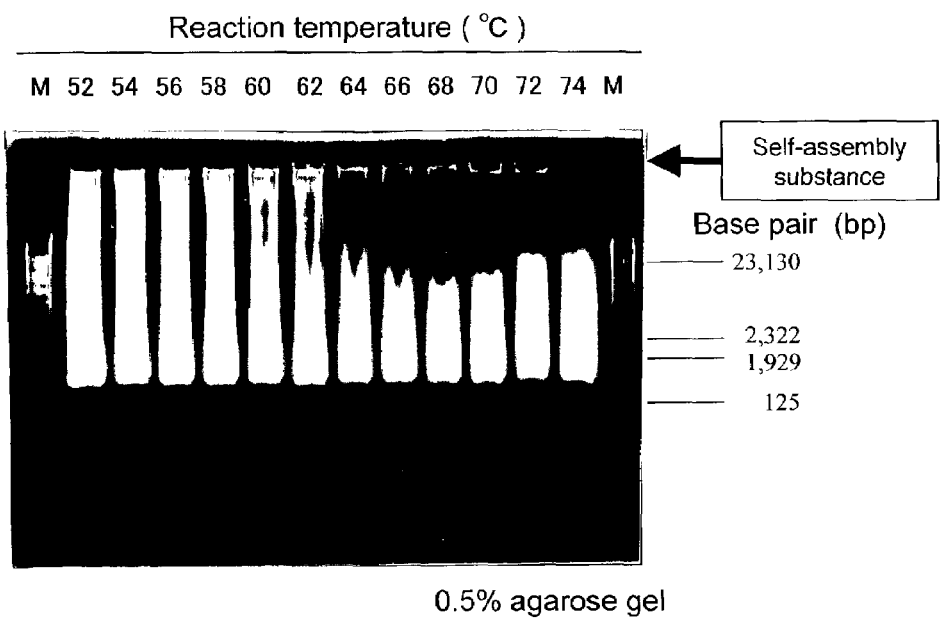
FIG. 16 is a photograph showing result of Inventive example 3.

As shown in a photograph of FIG. 16, even when 6 types of dimer forming probes, which form three sets of dimer-probes, were used, formation of the self-assembly substance was observed like Inventive example 1 and Inventive example 2 in which two sets of dimer-probes were used.

Capability of Exploitation in Industry:

As described above, according to the method for forming the self-assembly substance of the present invention, it is possible to shorten a reaction time for formation of the self-assembly substance as compared to the previous method. Also according to the method for detecting the self-assembly substance according to the present invention, it is possible to easily detect the self-assembly substance formed by the method for forming the self-assembly substance described above.

The invention claimed is:

1. A method for forming a self-assembly substance comprising the steps of:

providing a first group and a second group, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, wherein the pair of dimer forming probes for the first group and the second group are different, and wherein (a) the 3' side region of the oligonucleotide No. 1 of the first group and the 3' side region of the oligonucleotide No. 2 of the second group, (b) the 5' side region of the oligonucleotide No. 2 of the first group and the 5' side region of the oligonucleotide No. 1 of the second group, (c) the 3' side region of the oligonucleotide No. 1 of the second group and the 3' side region of the oligonucleotide No. 2 of the first group, and (d) the 5' side region of the oligonucleotide No. 2 of the second group and the 5' side region of the oligonucleotide No. 1 of the first group, have base sequences complementary to each other, respectively;

providing formed dimer-probes prepared by previously hybridizing a plurality of pairs of the dimer forming probes of the first and second groups to form the dimer-probes;

hybridizing the formed dimer-probes of each group; and forming a double-stranded self-assembly substance by self-assembly of the oligonucleotides.

2. A method for forming a self-assembly substance comprising the steps of:

providing a first group and a second group, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, wherein the pair of dimer forming probes for the first group and the second group are different, and wherein (a) the 3' side region of the oligonucleotide No. 1 of the first group and the 3' side region of the oligonucleotide No. 1 of the second group, (b) the 5' side region of the oligonucleotide No. 2 of the first group and the 5' side region of the oligonucleotide No. 1 of the second group, (c) the 3' side region of the oligonucleotide No. 2 of the second group and the 3' side region of the oligonucleotide No. 2 of the first group, and (d) the 5' side region of the oligonucleotide No. 2 of the second group and the 5' side region of the oligonucleotide No. 1 of the first group, have base sequences complementary to each other, respectively;

providing formed dimer-probes prepared by previously hybridizing a plurality of pairs of the dimer forming probes of the first and second groups to form the dimer-probes;

hybridizing the formed dimer-probes of each group; and forming a double-stranded self-assembly substance by self-assembly of the oligonucleotides.

3. A method for forming a self-assembly substance comprising the steps of:

providing plural groups from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, wherein all of the dimer-probes of plural groups are different, and wherein (a) the 3' side region of the oligonucleotide No. 1 of the (n−1)th group and the 3' side region of the oligonucleotide No. 2 of the nth group, (b) the 5' side region of the oligonucleotide No. 2 of the (n−1)th group and the 5' side region of the oligonucleotide No. 1 of the nth group, (c) the 3' side region of the oligonucleotide No. 1 of the last group and the 3' side region of the oligonucleotide No. 2 of the first group, and (d) the 5' side region of the oligonucleotide No. 2 of the last group and the 5' side region of the oligonucleotide No. 1 of the first group, have base sequences complementary to each other, respectively;

providing formed dimer-probes prepared by previously hybridizing a plurality of pairs of the dimer forming probes of the first group to the nth group to form the dimer-probes;

hybridizing the formed dimer-probes of each group; and forming a double-stranded self-assembly substance by self-assembly of the oligonucleotides.

4. A method for forming a self-assembly substance comprising the steps of:

providing plural groups from a first group to an nth (n is an even number of 2 or more) group in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and the 3' side regions and the 5' side regions of the oligonucleotides No.1 and No. 2 have base sequences not complementary to each other, and wherein (a) the 3' side region of the oligonucleotide No. 1 of the (n−1)th group and the 3' side region of the oligonucleotide No. 2 of the nth group, (b) the 5' side region of the oligonucleotide No. 1 of the (n−1)th group and the 5' side region of the oligonucleotide No. 2 of the nth group, (c) the 3' side region of the oligonucleotide No. 1 of the last group and the 3' side region of the oligonucleotide No. 2 of the first group, and (d) the 5' side region of the oligonucleotide No. 1 of the last group and the 5' side region of the oligonucleotide No. 2 of the first group, have base sequences complementary to each other, respectively;

hybridizing a plurality of pairs of the dimer forming probes of the first group to the nth group to form the dimer-probes;

hybridizing the formed dimer-probes of each group; and forming a double-stranded self-assembly substance by self-assembly of the oligonucleotides.

5. A method according to claim 1, wherein at least one G (guanine) or C (cytosine) is arranged at both ends of each one of the three regions of the dimer forming probes, and in hybridizing the dimer forming probes, at least one G-C bond is formed at all of the ends of the regions, thereby forming a stable double-stranded self-assembly substance.

6. A method according to claim 2, wherein at least one G (guanine) or C (cytosine) is arranged at both ends of each one of the three regions of the dimer forming probes, and in hybridizing the dimer forming probes, at least one G-C bond is formed at all of the ends of the regions, thereby forming a stable double-stranded self-assembly substance.

7. A method according to claim 3, wherein at least one G (guanine) or C (cytosine) is arranged at both ends of each one of the three regions of the dimer forming probes, and in hybridizing the dimer forming probes, at least one G-C bond is formed at all of the ends of the regions, thereby forming a stable double-stranded self-assembly substance.

8. A method according to claim 4, wherein at least one G (guanine) or C (cytosine) is arranged at both ends of each one of the three regions of the dimer forming probes, and in hybridizing the dimer forming probes, at least one G-C bond is formed at all of the ends of the regions, thereby forming a stable double-stranded self-assembly substance.

9. A method according to claim 1, wherein the dimer forming probes are composed of DNA, RNA, PNA and/or LNA.

10. A method according to claim 2, wherein the dimer forming probes are composed of DNA, RNA, PNA and/or LNA.

11. A method according to claim 3, wherein the dimer forming probes are composed of DNA,RNA, PNA and/or LNA.

12. A method according to claim 4, wherein the dimer forming probes are composed of DNA, RNA, PNA and/or LNA.

13. A set of dimer-probes comprising a dimer-probe of a first group and a dimer-probe of a second group, wherein each group is formed by hybridizing a pair of dimer forming probes, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and all of the 3' side regions and the 5' side regions of the oligonucleotides No.1 and No. 2 have base sequences not complementary to each other, wherein the pair of dimer forming probes for the first group and the second group are different, and wherein
    (a) the 3' side region of the oligonucleotide No. 1 of the first group and the 3' side region of the oligonucleotide No. 2 of the second group,
    (b) the 5' side region of the oligonucleotide No. 2 of the first group and the 5' side region of the oligonucleotide No. 1 of the second group,
    (c) the 3' side region of the oligonucleotide No. 1 of the second group and the 3' side region of the oligonucleotide No. 2 of the first group, and
    (d) the 5' side region of the oligonucleotide No. 2 of the second group and the 5' side region of the oligonucleotide No. 1 of the first group,
have base sequences complementary to each other, respectively.

14. A set of dimer-probes comprising a dimer-probe of a first group and a dimer-probe of a second group, wherein each group is formed by hybridizing a pair of dimer forming probes, wherein each group includes a pair of dimer forming probes containing a pair of oligonucleotides No. 1 and No. 2, in which the mid-regions of the oligonucleotides No.1 and No.2 have base sequences complementary to each other, and all of the 3' side regions and the 5' side regions of the oligonucleotides No.1 and No. 2 have base sequences not complementary to each other, wherein the pair of dimer forming probes for the first group and the second group are different, and wherein
    (a) the 3' side region of the oligonucleotide No. 1 of the first group and the 3' side region of the oligonucleotide No. 1 of the second group,
    (b) the 5' side region of the oligonucleotide No. 2 of the first group and the 5' side region of the oligonucleotide No. 1 of the second group,
    (c) the 3' side region of the oligonucleotide No. 2 of the second group and the 3' side region of the oligonucleotide No. 2 of the first group, and
    (d) the 5' side region of the oligonucleotide No. 2 of the second group and the 5' side region of the oligonucleotide No. 1 of the first group,
have base sequences complementary to each other, respectively.

15. A set of dimer-probes of plural groups comprising a dimer-probe of a first group and an nth group of dimer-probes (n is an even number of 2 or more), wherein each group if formed by hybridizing a pair of dimer forming probes in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and all of the 3' side regions and the 5' side regions of the oligonucleotides No.1 and No. 2 have base sequences not complementary to each other, wherein all of the dimer-probes of plural groups are different, and wherein
    (a) the 3' side region of the oligonucleotide No. 1 of the (n−1)th group and the 3' side region of the oligonucleotide No. 2 of the nth group,
    (b) the 5' side region of the oligonucleotide No. 2 of the (n−1)th group and the 5' side region of the oligonucleotide No. 1 of the nth group,
    (c) the 3' side region of the oligonucleotide No. 1 of the last group and the 3' side region of the oligonucleotide No. 2 of the first group, and
    (d) the 5' side region of the oligonucleotide No. 2 of the last group and the 5' side region of the oligonucleotide No. 1 of the first group,
have base sequences complementary to each other, respectively.

16. A set of dimer-probes of plural groups comprising a dimer-probe of a first group and an nth group of dimer-probes n is an even number of 2 or more), wherein each group is formed by hybridizing a pair of dimer forming probes in turn, wherein each group includes a pair of dimer forming probes containing a pair of oligonucleotides No. 1 and No. 2, each oligonucleotide having three regions of a 3' side region, a mid-region and a 5' side region, in which the mid-regions of the oligonucleotides No.1 and No.2 have base sequences complementary to each other, and all of the 3' side regions and the 5' side regions of the oligonucleotides No.1 and No. 2 have base sequences not complementary to each other, wherein all of the dimer-probes of plural groups are different, and wherein
    (a) the 3' side region of the oligonucleotide No. 1 of the (n−1)th group and the 3' side region of the oligonucleotide No. 2 of the nth group,
    (b) the 5' side region of the oligonucleotide No. 1 of the (n−1)th group and the 5' side region of the oligonucleotide No. 2 of the nth group,
    (c) the 3' side region of the oligonucleotide No. 1 of the last group and the 3' side region of the oligonucleotide No. 2 of the first group, and
    (d) the 5' side region of the oligonucleotide No. 1 of the last group and the 5' side region of the oligonucleotide No. 2 of the first group,
have base sequences complementary to each other, respectively.

* * * * *